(12) United States Patent
Kim et al.

(10) Patent No.: US 10,456,553 B2
(45) Date of Patent: *Oct. 29, 2019

(54) DEVICE AND METHODS FOR TARGETED TISSUE DRUG DELIVERY

(71) Applicant: NATIVE CARDIO, INC., Naples, FL (US)

(72) Inventors: Young D. Kim, Circle Mclean, VA (US); Joseph V. Pergolizzi, Naples, FL (US); Scot Johnson, Tampa, FL (US)

(73) Assignee: Native Cardio, Inc., Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/133,977

(22) Filed: Sep. 18, 2018

(65) Prior Publication Data

US 2019/0083742 A1    Mar. 21, 2019

Related U.S. Application Data

(63) Continuation of application No. 14/427,607, filed as application No. PCT/US2013/058814 on Sep. 9, 2013, now Pat. No. 10,118,014.

(60) Provisional application No. 61/749,713, filed on Jan. 7, 2013, provisional application No. 61/743,759, filed on Sep. 11, 2012.

(51) Int. Cl.
| | | |
|---|---|---|
| *A61N 1/05* | (2006.01) | |
| *A61M 25/00* | (2006.01) | |
| *A61M 19/00* | (2006.01) | |
| *A61N 1/04* | (2006.01) | |

(52) U.S. Cl.
CPC ....... *A61M 25/0023* (2013.01); *A61N 1/0587* (2013.01); *A61N 1/0597* (2013.01); *A61M 19/00* (2013.01); *A61M 2025/0004* (2013.01); *A61N 1/046* (2013.01); *A61N 1/0476* (2013.01); *A61N 1/0595* (2013.01)

(58) Field of Classification Search
CPC .............. A61M 25/0023; A61M 19/00; A61M 2025/0004; A61N 1/0597; A61N 1/0587; A61N 1/0595; A61N 1/046; A61N 1/0476
See application file for complete search history.

(56) References Cited

U.S. PATENT DOCUMENTS

| | | | |
|---|---|---|---|
| 7,270,669 B1 | 9/2007 | Sra | |
| 2003/0036773 A1 | 2/2003 | Whitehurst et al. | |
| 2003/0233128 A1* | 12/2003 | Kim ..................... | A61N 1/3962 607/5 |
| 2005/0113760 A1 | 5/2005 | Chachques et al. | |
| 2005/0215991 A1 | 9/2005 | Altman et al. | |
| 2009/0069789 A1 | 3/2009 | Freyman et al. | |

(Continued)

FOREIGN PATENT DOCUMENTS

| | | |
|---|---|---|
| WO | 2009006337 | 1/2009 |
| WO | 2009099597 | 8/2009 |

OTHER PUBLICATIONS

The International Search Report dated Mar. 20, 2014 for International Application No. PCT/US2013/058814, 2 pgs.

*Primary Examiner* — Amanda K Hulbert
*Assistant Examiner* — Natasha Patel
(74) *Attorney, Agent, or Firm* — Lowenstein Sandler LLP

(57) ABSTRACT

Representative embodiments of the present invention provide for novel, minimally invasive implantable devices and methods for targeted tissue drug delivery of cardiovascular drugs.

19 Claims, 20 Drawing Sheets

(56) References Cited

U.S. PATENT DOCUMENTS

2009/0287166 A1* 11/2009 Dang .................... A61M 25/00
                                                    604/265
2013/0218124 A1    8/2013  Imran et al.

* cited by examiner

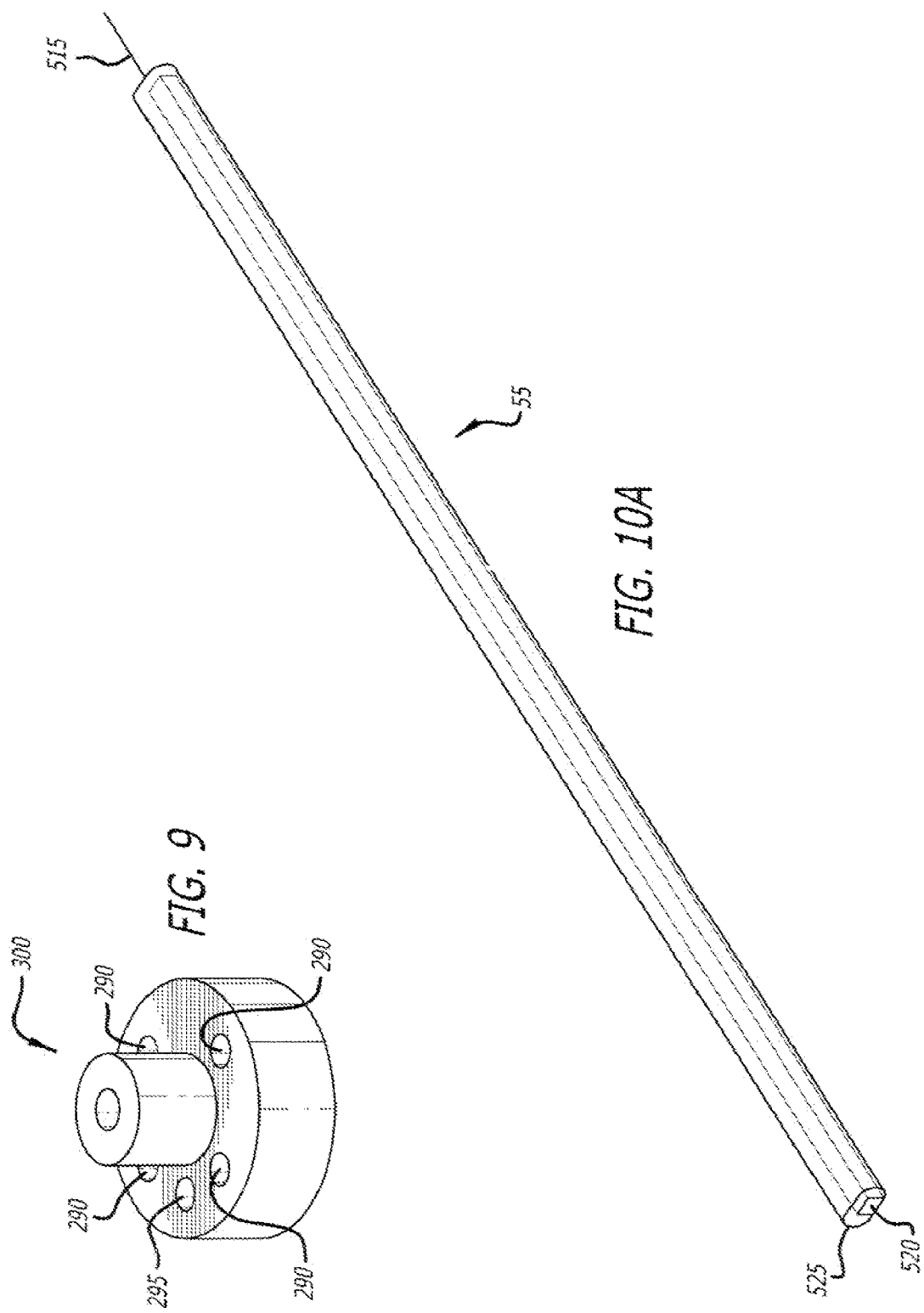

DEVICE AND METHODS FOR TARGETED TISSUE DRUG DELIVERY

CROSS-REFERENCE TO RELATED APPLICATIONS

This PCT international patent application claims priority to U.S. Provisional Patent Application 61/743,759 filed Sep. 11, 2012, and U.S. Provisional Patent Application 61/749,713 filed Jan. 7, 2013, the entire contents of which are incorporated herein by reference.

FIELD OF THE INVENTION

The general subject matter of this invention relates to novel, minimally invasive implantable devices and methods for targeted tissue drug delivery.

BACKGROUND

Cardiac rhythm disturbances, for instance, atrial fibrillation are a frequent occurrence. Current practice usually dictates pharmacological treatments and/or electrical shock conversion for treatment of patients. Conventional pharmacological treatment of cardiac rhythm disturbances often fails and requires electrical shock conversion. Electrical shock conversion requires a high amount of energy and maintaining the sinus rhythm using this approach has proven to be quite difficult. Moreover, conventional approaches pose additional problems for treatment of patients suffering from abnormal cardiac rhythms.

Hemodynamic instability from atrial fibrillation or failure of pharmacological treatment of atrial fibrillation mandates electric shock defibrillation. Conventional external electric defibrillation procedures typically require high electrical energy (i.e., on the order of 50-150 joules) and, as a result of the intense shock and patient discomfort associated therewith, are typically delivered after general anesthesia or deep sedation, both of which are time consuming procedures. In addition, the high amount of energy required to place a patient back into sinus rhythm requires costly drugs for sedation and can cause external skin damage and pain. Moreover, external shock defibrillation is a time consuming process requiring extra man power in the form of anesthesiologists, cardiologist, and nurses. Finally, the procedure itself is not without substantial risk; the human cost associated with external shock can include disturbing cardiac liability to the point where the patient may die. The numerous complications, disadvantages and failures associated with conventional systemic use of antiarrhythmic drugs and external electrical shock procedures has prompted many attempts to significantly improve treatment and patient care.

Moreover, there is also a significant and long-felt but yet unmet need for reducing and eliminating systemic toxicity associated with conventional, systemic drug treatment of patients suffering from cardiac rhythm disturbances. High doses of drugs typically need to be administered systemically, e.g., by the oral or intravenous delivery methods, to achieve sufficient levels within the heart tissue in order for the drug treatment to have any effect. However, these high doses of drugs are generally unacceptable due to systemic side effects. Thus, a significant need exists for treatment of patients which does not suffer whole systemic toxicity associated with systemic delivery.

Conventional treatments for chronic atrial fibrillation (AF), such as for example surgical treatments and cardiac abrasions (radiofrequecy, cryoabrasion), are often associated with grave, problematic and serious complications including, for instance, bleeding, perforations, scar-stricture and even death.

In addition, temporary treatments do not address the significant population of patients that suffer long-term from chronic cardiac rhythm disturbances. Unlike the invention described in U.S. Pat. No. 6,965,798, which is directed solely to the temporary treatment of atrial rhythm disturbances in postoperative cardiac patients, there still remains a significant, long-felt and yet unmet need for safe and effective long-term treatment of patients suffering from chronic or long-term abnormal cardiac rhythms. A significant, long-felt and yet unmet need exists for new modes of treatments for chronic atrial fibrillation. These new treatments are needed in order to improve or eliminate problems of current treatments such as systemic drug toxicity, high electric energy requirements for cardioversion and high invasiveness.

SUMMARY

The representative embodiments of the present invention described herein relate to novel, minimally invasive implantable devices and methods for targeted tissue drug delivery for cardiovascular drugs.

These and other features, aspects, and advantages of the present invention will become more apparent from the following description, appended claims, and exemplary embodiments shown its the drawings and also described herein.

The embodiments described herein are examples, and shall not be construed in any way as limiting the scope of the invention.

BRIEF DESCRIPTION OF THE DRAWINGS

The accompanying drawings, which are disclosed and described herein, illustrate various embodiments of the invention. The embodiments described herein are examples, and shall not be construed in any way as limiting the scope of the invention.

The dimensions of the components of the novel minimally invasive implantable device are not shown in an exact scale, and are intended to be scalable.

FIG. 9 depicts one representative embodiment of a connecting portion 300.

FIGS. 10A-10B depict one representative embodiment of a leaflet 55.

FIG. 16B shows a representative cross-sectional view of the device shown in FIG. 16A.

Figure 1:
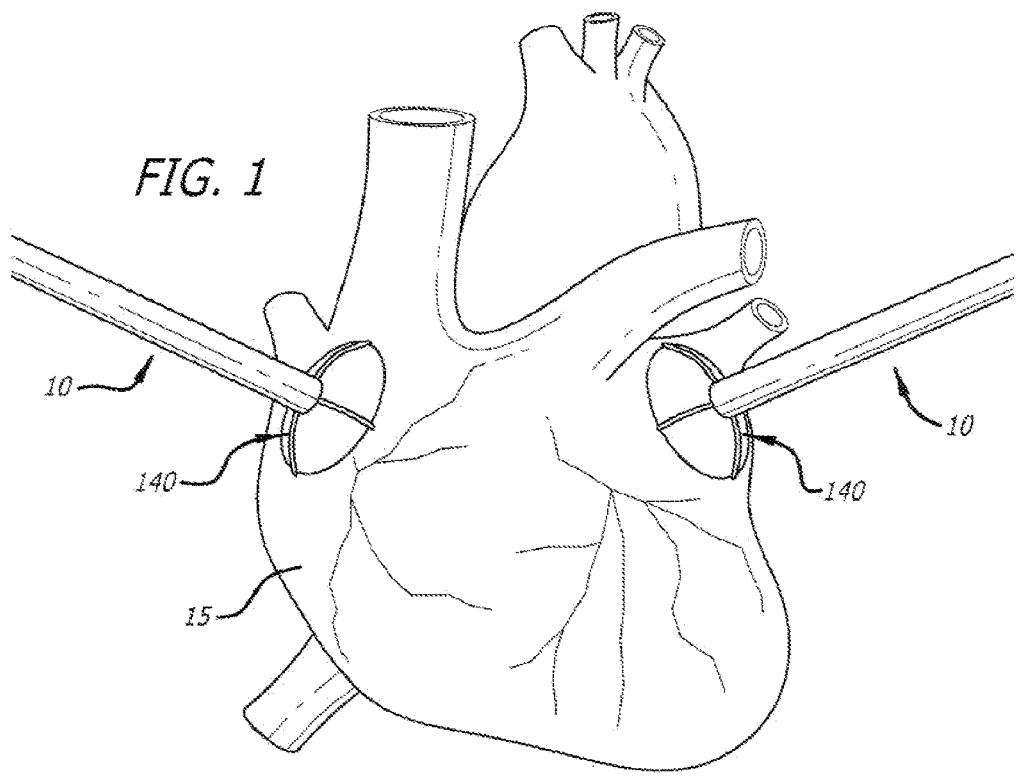
FIG. 1 shows one embodiment of the present invention, in which a plurality of interface devices 10 have been placed in contact with the front of the heart 15.

Other embodiments and further details regarding various aspects of the present invention are set forth in the following description and claims. It is to be understood that the invention is not limited in its application to the details set forth in the following description and claims, but is capable of other embodiments and of being practiced or carried out in various ways.

DESCRIPTION OF REPRESENTATIVE EMBODIMENTS

Representative embodiments of the present invention are described and depicted herein for illustrative purposes, and in no way whatsoever limit the scope of the present invention. It is to be understood that all references cited herein in this disclosure are incorporated herein by reference in their entirety.

The long-felt and yet unmet need to prevent extra-cardiac effects associated with systemic toxicity (which is associated with conventional oral or intravenous administration of drugs) in the patient has led to efforts to pursue different ways to administer these agents to the patient in need of treatment. The present invention provides a number of surprising and unexpected benefits as a result of the novel devices and methods (as described herein) for local and targeted application of antiarrhythmic drugs. In particular, one of the surprising benefits of the present invention is the reduction or elimination of systemic toxicity as a result of the targeted delivery of pharmaceutical agents or drugs to the heart, using the device and methods of the present invention. The rationale for local, targeted drug delivery, as contemplated by the present invention, is that a relatively high proportion of the drug will be delivered to the cardiac tissue, resulting in a therapeutic response at a significantly lower dose. The lower dose translates into a significantly lower systemic drug level, thus minimizing or eliminating extra-cardiac effects associated with conventional systemic toxicity. In accordance with the present invention, one or more antiarrhythmic drugs and/or other suitable pharmaceutical agents can be delivered directly to the heart, including for example delivery to the intrapericardial space (the fluid sac surrounding the heart), the atria, and the AV node.

Utilizing the device and methods of the present invention, there are additional surprising and unexpected advantages to local, targeted drug delivery to the heart. This type of local, targeted drug delivery can restore sinus rhythm and prevent atrial fibrillation (AF) using much lower doses (for example, 100× less), as compared to conventional practices. This in turn alleviates or removes the unwanted systemic side effects associated with conventional administration of the drugs. In addition, in accordance with the present invention, the relatively lower energy (fewer joules required) that is required is successful in restoring sinus rhythm by using significantly less energy than conventional external defibrillation processes. This in turn eliminates the need for sedation, anesthesiologists, and also significantly lessens the pain felt by the patient. Moreover, use of the device in a minimally invasive manner significantly reduces the pain and discomfort to the patient.

According to the present invention, and as described further herein, the amount of drug delivered, as well as the drug type, timing, frequency, and dosage, can be controlled as needed or desired. For instance, the amount of drug delivered, as well as the timing, frequency and dosage, can be increased or decreased in response to changes in a patient's condition.

Also, as further described herein, the methods and apparatus of the present invention have a number of surprising and unexpected advantages, including, but not limited to, (a) successfully defibrillating an atrium while delivering a quantum of energy that a conscious and non-sedated patient will either not notice or easily tolerate; (b) eliminating (or at least minimising) the side effects caused by systemic exposure to high doses of antiarrhythmic drugs, by delivering antiarrhythmic medication directly to the atria; and (c) controlling drug delivery directly to the atria in terms of drug type, timing, and/or dosage. Moreover, the methods and apparatus of the present invention provide novel and unexpected advantages due to the ability to provide asymmetric delivery of drugs to the heart.

In certain embodiments, one or more drugs may also be continuously delivered to the atrial surface by means of a pump. While one or more drugs are being administered to the patient, via the device of the present invention, electrical defibrillation shocks can also be provided to the heart of the patient.

Unlike conventional external electrical shock which requires 50-150 joules of energy much of which is absorbed by the torso of the patient according to the present invention, a significantly smaller amount of energy (e.g., such as between about 1.0 and 3.0 joules, and preferably leas than about 2.0 joules) will be needed to defibrillate the right and left atria.

More preferably, according to the present invention, less than one (1) joule is sufficient to provide electrical defibrillation energy to the heart of the patient, to achieve a desired clinical effect. Thus, in preferred embodiments, an even smaller amount of energy (e.g., between zero to about 1.0 joules, and preferably less than about 2.0 joules) will be needed to achieve a desired clinical effect, i.e., so defibrillate the right and/or the left atria.

This amount of energy will cause the patient nearly no discomfort and, therefore, can be administered without anesthesia or sedation. Moreover, the cost of the present invention for treating patients is minimal compared to conventional approaches, including electrical shock conversion for treatment of patients. In addition, the device of the present invention is minimally invasive; and such placement within the patient does not require a complex delivery system.

According to certain preferred embodiments of the present invention, the novel minimally invasive implantable device can be used in acute cases (patients suffering from acute cases of abnormal cardiac rhythms). According to other preferred embodiments, the novel minimally invasive implantable device can be used in chronic cases, in which patients suffering from chronic abnormal cardiac rhythms can be assisted by the novel minimally invasive implantable device of the present invention which interfaces the heart and transfers either electrical, chemical, or both forms of atrial defibrillation. In either the acute case or chronic case, the novel minimally invasive implantable device transfers either electrical, chemical, or both to the atria to facilitate defibrillation. The minimally invasive implantable device also surprisingly and unexpectedly allows for lower electrical power and/or lower concentrations of pharmaceutical agent(s) as compared to conventional, external defibrillation means.

All ranges disclosed herein are to be understood to encompass any and all subranges included therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

As used herein, the term "abnormal cardiac rhythms" is intended to refer, but is not limited to, any type of cardiac arrhythmia or abnormal heart rhythm. It is to be understood that other examples of "abnormal cardiac rhythms" are encompassed within the scope of the present invention.

Unless defined otherwise, all technical and scientific terms used herein have the same meaning as commonly understood by one of ordinary skill in the art.

As described herein, the present invention comprises novel devices and methods for achieving targeted tissue drug delivery for cardiovascular drugs.

As used herein, the term "interface device" and device", for example, "interface device 10" and "device 10" are sometimes used interchangeably in the description of the present invention, and it is to be understood that these terms are intended to refer to the same device.

As used herein, the term "minimally invasive" is intended to refer to a procedure for minimally invasive implantation of a device in accordance with the present invention. Minimally invasive implantation is a procedure that involves as little discomfort so the patient as possible, and which does not interfere with normal activities of the patient, in particularly in cases in which the device is implanted long-term in the patient, e.g., for treatment of chronic conditions including chronic cases of cardiac arrhythmias or other chronic cases of cardiac rhythm disturbances.

As used herein, the term "acute case" is intended to include, but is not limited to, patients suffering from one or more cases of abnormal cardiac rhythms that have a relatively shore duration, such as an acute episode.

As used herein, the term "chrome case" is intended to include, but is not limited to, patients suffering from one or more cases of abnormal cardiac rhythms that last for a prolonged duration, for instance, patients suffering from chronic abnormal cardiac rhythms.

As used herein, the term "electrical defibrillation" is intended to refer, but is not limited to, delivery of electrical charge to the heart, in accordance with the present invention, in order to treat cases of cardiac arrhythmias or other cases of cardiac rhythm disturbances. While the embodiments discuss "defibrillation" the inventors expressly anticipate using the invention to also provide pacing therapy. According to certain examples, the electrical energy delivered so the heart (for example, an atrial surface) may be from about 1.0 joules to about 3.0 joules.

As described elsewhere herein, in preferred embodiments, according to the present invention, less than one (1) joule is sufficient to provide electrical defibrillation energy to the heart of the patient, to achieve a desired clinical effect. Thus, in preferred embodiments, an even smaller amount of energy (e.g., between zero to about 1.0 joules, and preferably less than about 2.0 joules) will be needed to achieve a desired clinical effect, i.e., to defibrillate the right and/or the left atrium.

As used herein, the term "pharmaceutical agent" is intended to include any suitable pharmaceutical agent that can be administered to the heart of a patient, in accordance with the devices and methods of the present invention, to treat an abnormal cardiac rhythm or other cardiac condition. It is to be understood that the term pharmaceutical agent, as used herein, is intended to include, and therefore shall also be construed as also including, any and all pharmaceutically acceptable prodrugs, metabolites or derivatives of the pharmaceutical agent, and any and all pharmaceutically acceptable enantiomers, racemic forms, salt forms, free base forms, solvates, hydrates, hemihydrates, other hydrated forms, polymorphic or crystalline forms, isomorphs, or any other derivative thereof. Representative examples of at least one or more pharmaceutical agents, and/or any active prodrug, metabolite or derivative thereof that can be used in accordance with the present invention are provided in further detail herein.

Several embodiments are described herein for the present invention, and certain embodiments are described in U.S. Provisional Patent Application Ser. No. 61/743,759, the contents of which is incorporated by reference herein in its entirety. In certain embodiments, the novelty of the invention includes a unique interface between regions of the heart and either external or internal, electrical and/or chemical defibrillation generating/delivery devices. The novel invention provides, for example, and according to certain preferred embodiments, devices and methods by which electrical or chemical defibrillation is transferred to one or more affected regions of the heart. The novel invention includes either a singularly electrical defibrillation interface, a singularly chemical defibrillation interface, or both an electrical and chemical defibrillation interface. According to certain embodiments, additional uses of the novel invention include, for example, utilizing existing electrical connections or including an additional electrical connection for detecting the electrical signals of the heart.

Ideally, the novel interface is an implantable grade material or materials and is compatible with delivery of electrical power and intended pharmaceutical agents.

Certain representative embodiments of the novel device are described and shown in U.S. Provisional Patent Application Ser. No. 61/743,759, which is incorporated by reference herein in its entirety, and which can effectively be used in preferred embodiments for targeted tissue drug delivery of cardiovascular drugs.

FIG. 1 is a schematic view of a patient's heart showing two of the devices 10 positioned thereupon. Referring to FIG. 1, one embodiment of the present invention is shown, in which a plurality of interface devices 10 have been placed in contact with the front of the heart 15. The flower-like arrangement 140 of one of the devices 10 is adhered to the atrial surface of the right atrium, whereas the flower-like arrangement 140 of the other device 10 is adhered to the atrial surface of the left atrium.

Figure 2:
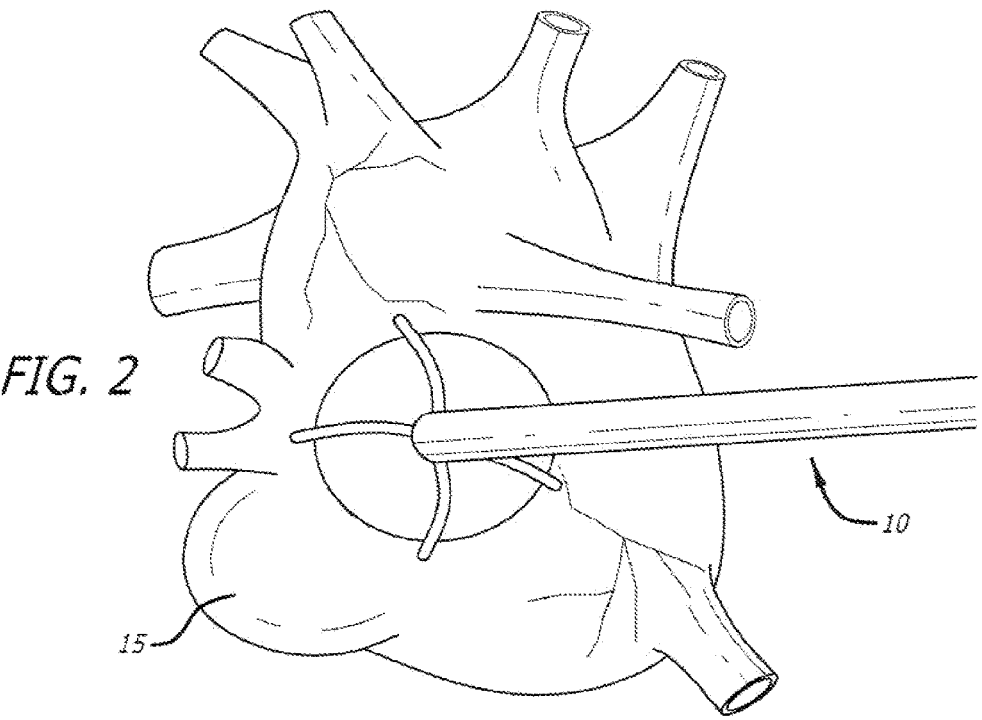
FIG. 2 depicts another embodiment, in which interface device 10 has been placed in contact with the back of the heart 15.

Referring to FIG. 2, another representative embodiment, of the present invention is shown, wherein an interface device 10 is placed in contact with the back of the heart 15, and more specifically over the region wherein the pulmonary veins are concentrated.

Referring again to FIGS. 1 and 2, it is to be understood that at least one or more interface devices 10 can be placed in contact with the heart. For example, one, two, three, four, or any other suitable number of interface devices 10 can be placed in contact with the heart. The actual number of interface devices 10 and the placement, location and orientation of the interface devices 10 in contact with the heart will typically be determined by many factors. These factors include, for example, the needs of the patient as determined by a healthcare professional, the clinical condition and diagnosis of the patient, and the overall professional opinion, evaluation and judgment of the patient's healthcare professional or team of professionals.

Figure 3A:
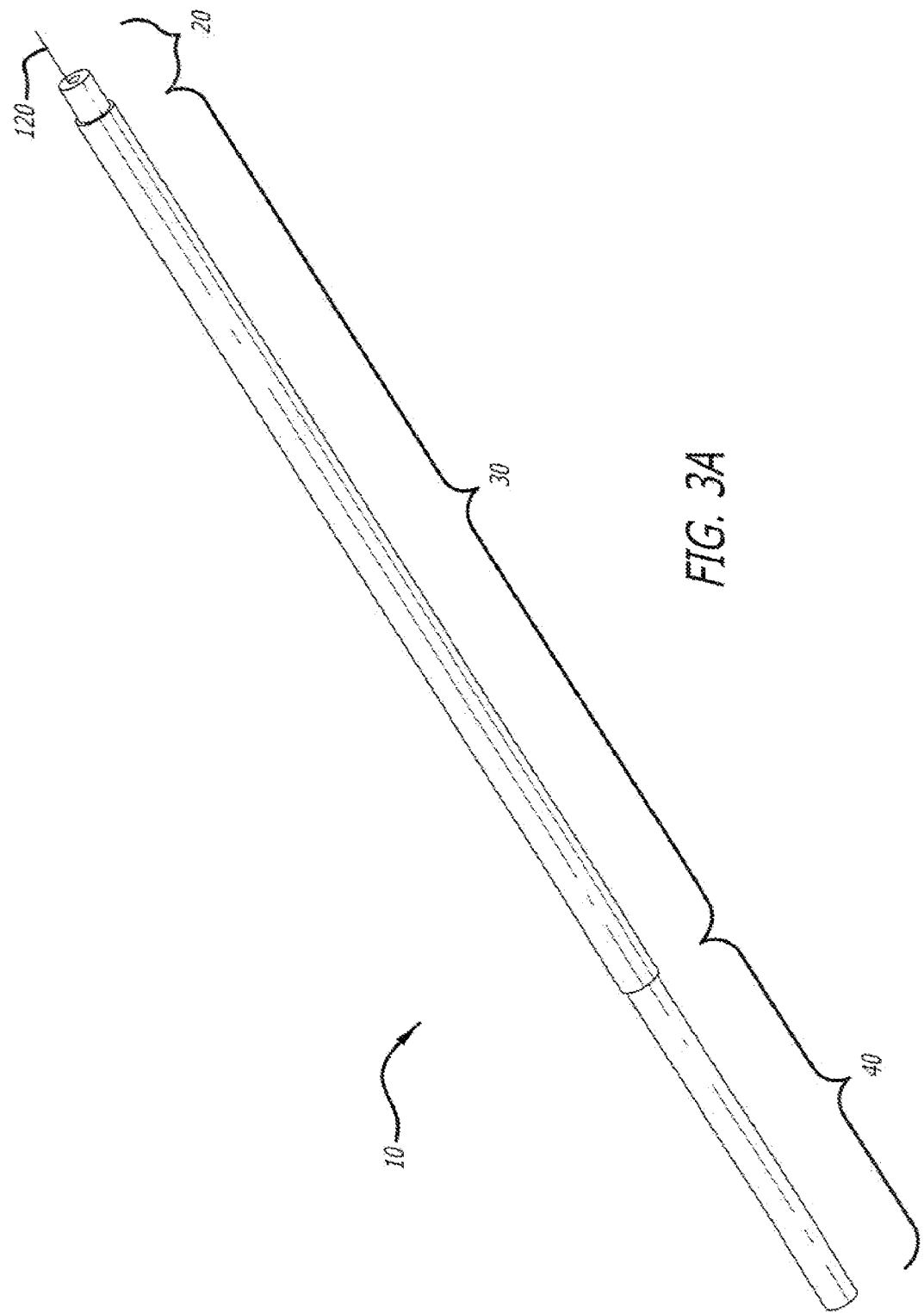
FIGS. 3A, 3B and 3C depict one representative embodiment of an interface device 10, before minimally invasive implantation into a patient.
Figure 3B:
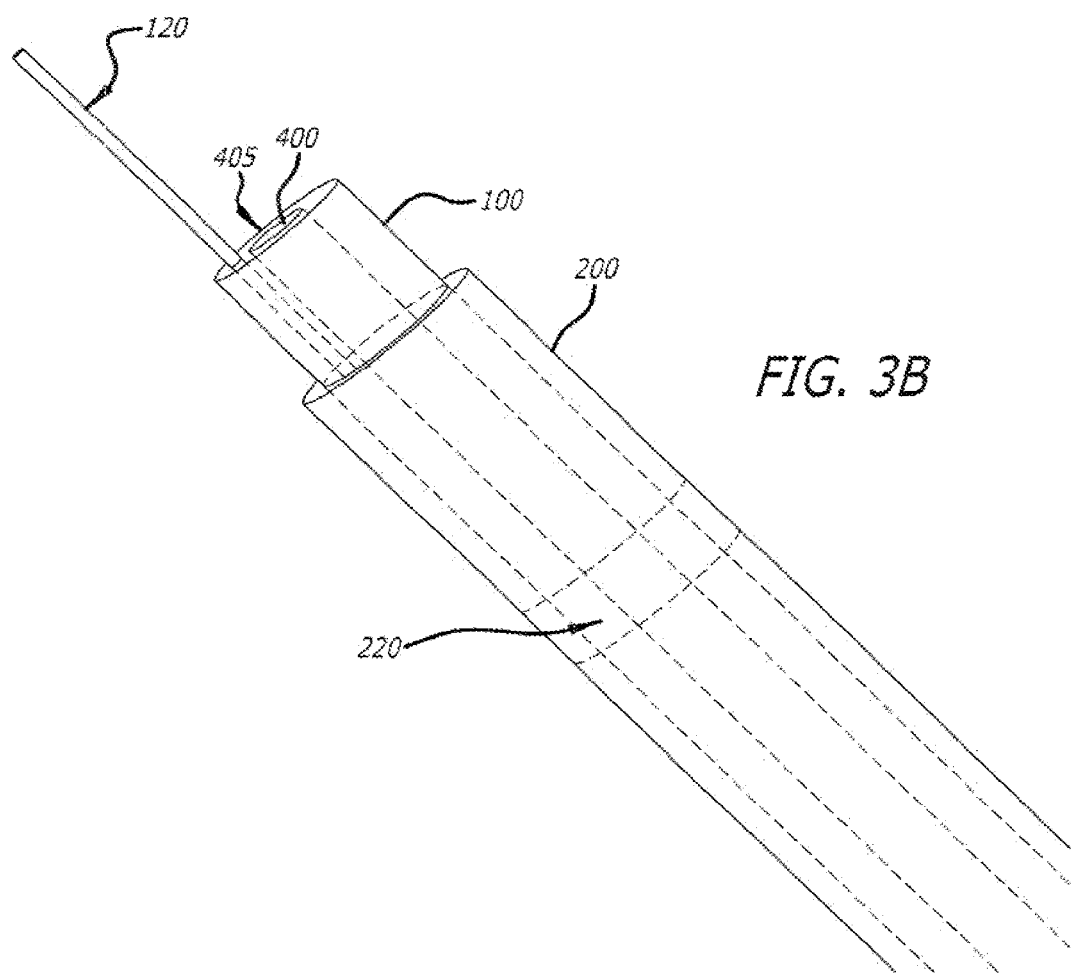
Figure 3C:
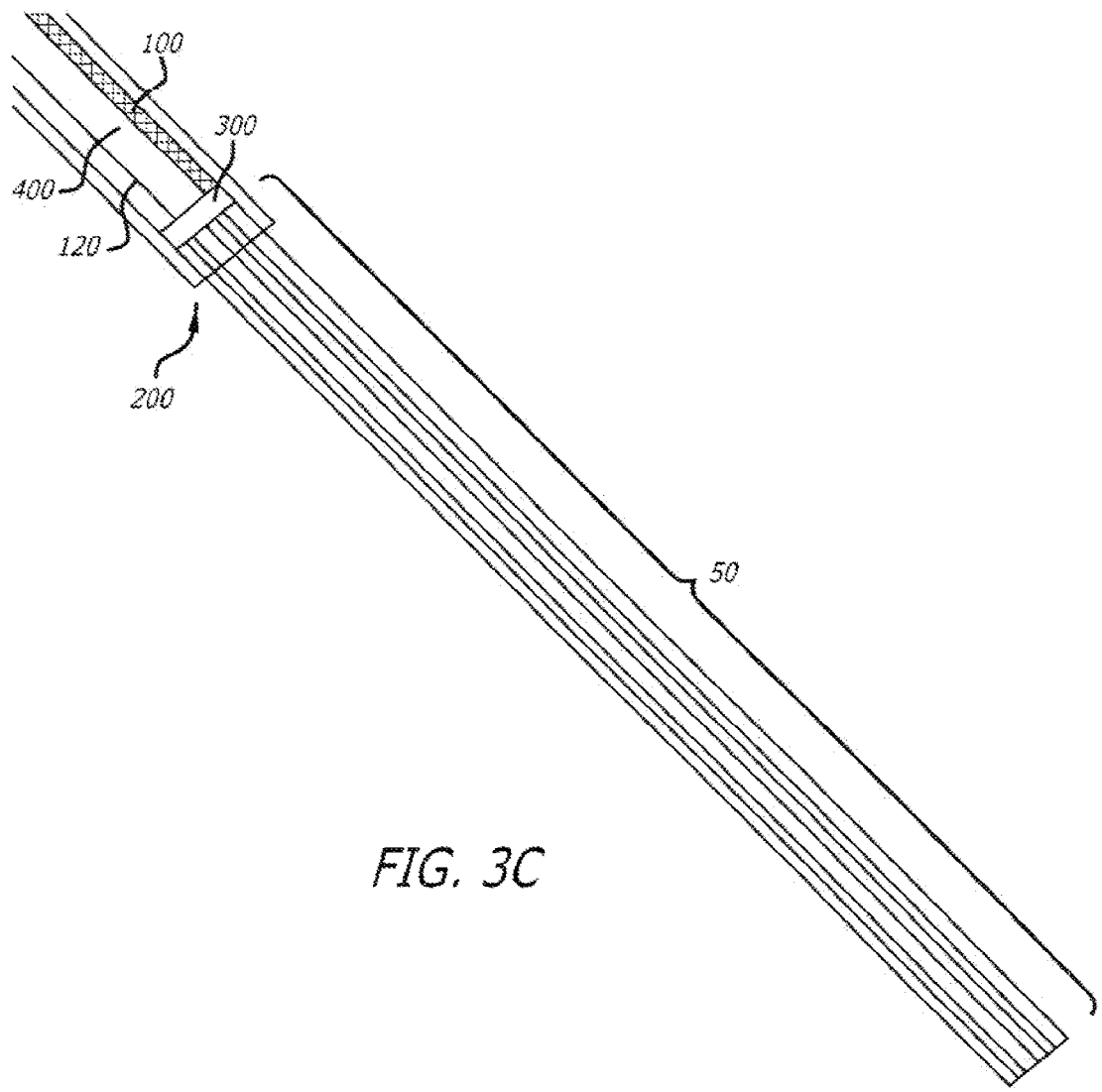

FIGS. 3A, 3B and 3C depict one representative embodiment of an interface device 10, before minimally invasive implantation of the device 10 into a patient.

According to this embodiment, and referring to FIG. 3A, the interface device 10 comprises a proximal portion 20, a central portion 30, and a distal portion 40. The proximal portion 20 of the device 10 is located outside the patient body. As described in greater detail herein, the distal portion 40 comprises leaflet assembly 50. It is to be understood that a single leaflet assembly 50 can comprise any suitable number of leaflets, for example, but not limited to, one, two, three, four, five, six or more leaflets 55, or any other suitable number or plurality of leaflets 55.

The proximal portion 20 is shown in further detail in FIG. 3B. Referring to FIG. 3B, the schematic represents one preferred configuration of the device, in particular, at a stage when the inner catheter 100 has not yet been pulled through the outer catheter 200 to retrieve the leaflet assembly 50. This is a preferred configuration before minimally invasive implantation of the device 10 into a patient.

FIG. 3B also depicts one example of an inner catheter conductor 120. The inner catheter conductor 120 can be made of one or more electrically conductive materials, for example, but not limited to, copper, and/or one or more other electrically conductive metals, or doped metals, alloys, or any combination thereof.

Figure 11A:
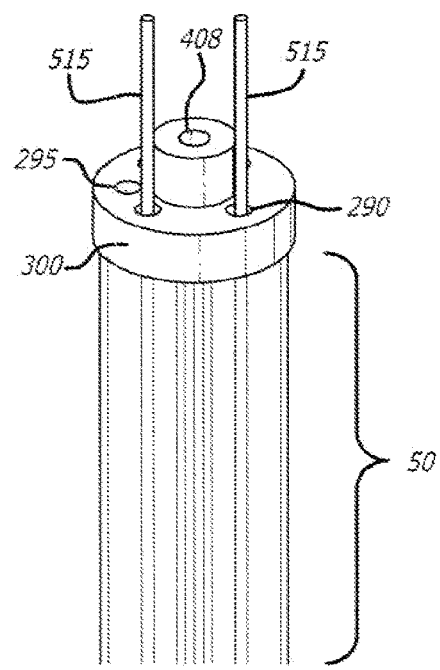
FIGS. 11A through 11E depict a series of diagrams that illustrate one representative process for construction of a distal portion 40 of an interface device 10.
Figure 11B:
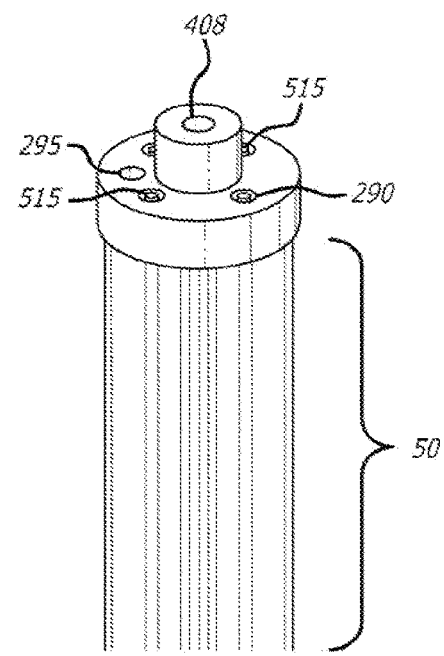
Figure 11C:
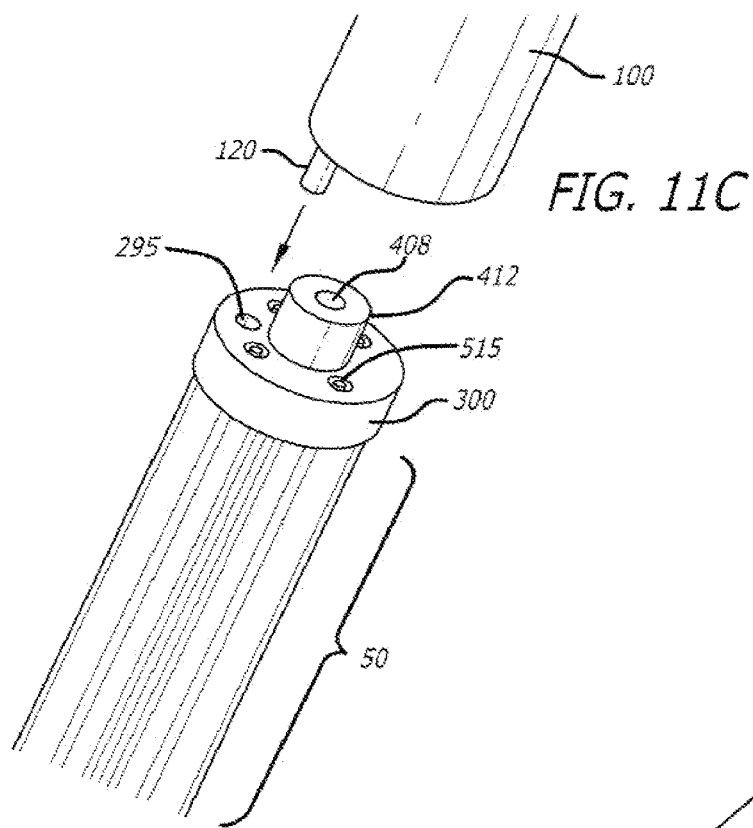
Figure 11D:
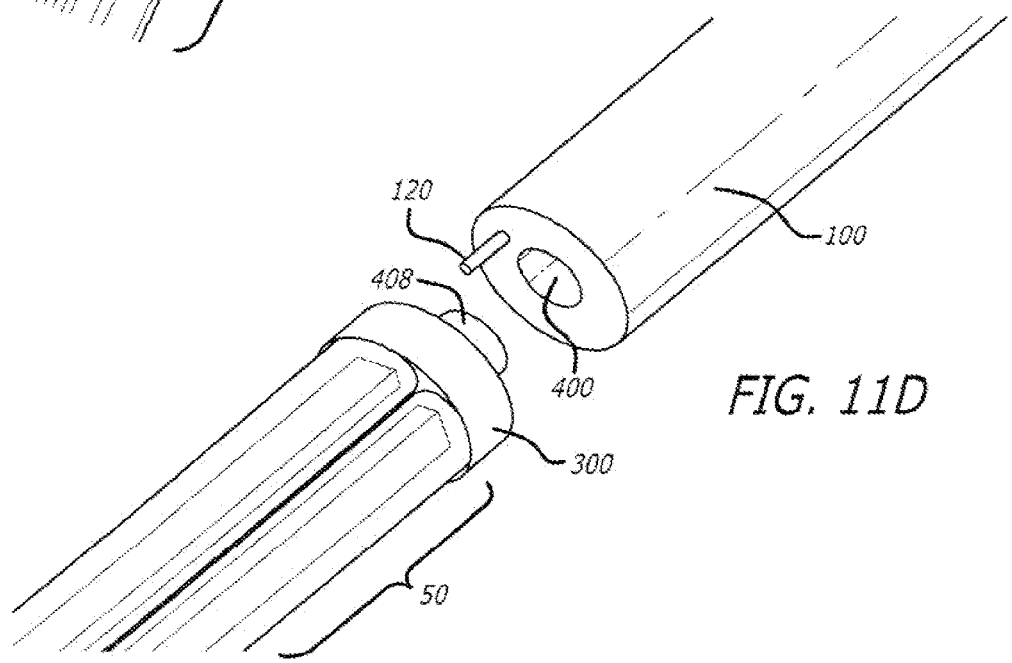

As depicted schematically in FIGS. 3B, 11C and 11D, the inner catheter conductor 120 may be provided within a lumen in the catheter 100. The inner catheter conductor 120 may be made of one or more electrically conductive wires and/or other conductive elements. Although not depicted in the accompanying figures, according to other embodiments, one or more additional conductors may also be provided within or along the inner catheter 100, in addition to the inner catheter conductor 120. The inner catheter conductor 120 is effective for providing electrical defibrillation to the heart of a patient by completing art electric circuit which evenly distributes electric charge among the leaflets 55 of the leaflet assembly 50.

In other embodiments (not shown), the inner catheter 100 can be designed to include any number of other conductive elements, in addition to the inner catheter conductor 120. For instance, the inner catheter 100 can be designed to include one, two, three, four, five or more additional conductive elements.

Referring again to the example shown in FIGS. 3A and 3B, the inner catheter conductor 120 extends through the entire length of the inner catheter 100. In this example, the inner catheter conductor 120 thus extends from the proximal portion 20, through the central portion 30, and then the inner catheter conductor 120 is inserted into one of the plurality of slots in the connecting portion 300, as further described with reference to FIGS. 11C, 11D, 11E and FIG. 12. The function and operation of the inner catheter conductor 120 will be described in further detail below, with reference to FIGS. 11C, 11D, 11E and FIG. 12.

As shown in FIG. 3B, according to another embodiment, an optional clamp 220 (position of the clamp is depicted schematically with dotted lines) can be placed around the outside of the outer catheter 200, which is positioned outside the patient's body. The optional clamp 220 can be loosened or removed as needed in order to assist in pulling the inner catheter 100 and distal portion 40 of the device 10 through the outer catheter 200.

Referring again to FIG. 3B and also FIG. 3C, there is shown the inner catheter 100, inner catheter conductor 120, outer catheter 200, connecting portion 300, drug delivery channel 400, and leaflet assembly 50. The inner catheter 100 and the outer catheter 200 can be made of any suitable material, for instance, teflon, silicone, suitable thermoplastic elastomer (TPE), plastic, and/or one or more other synthetic materials.

Referring again to FIG. 3B, and for case of reference and understanding, the catheters 100 and 200 are shown as being transparent. Preferably, the catheter 100 is insulated and formed of a synthetic material such as PVC or polyurethane. The catheter 100, which can for example be about 16 gauge in size, is preferably long enough to extend from an atrial surface of a patient to a location external of the patient's chest wall 40.

Figure 4:
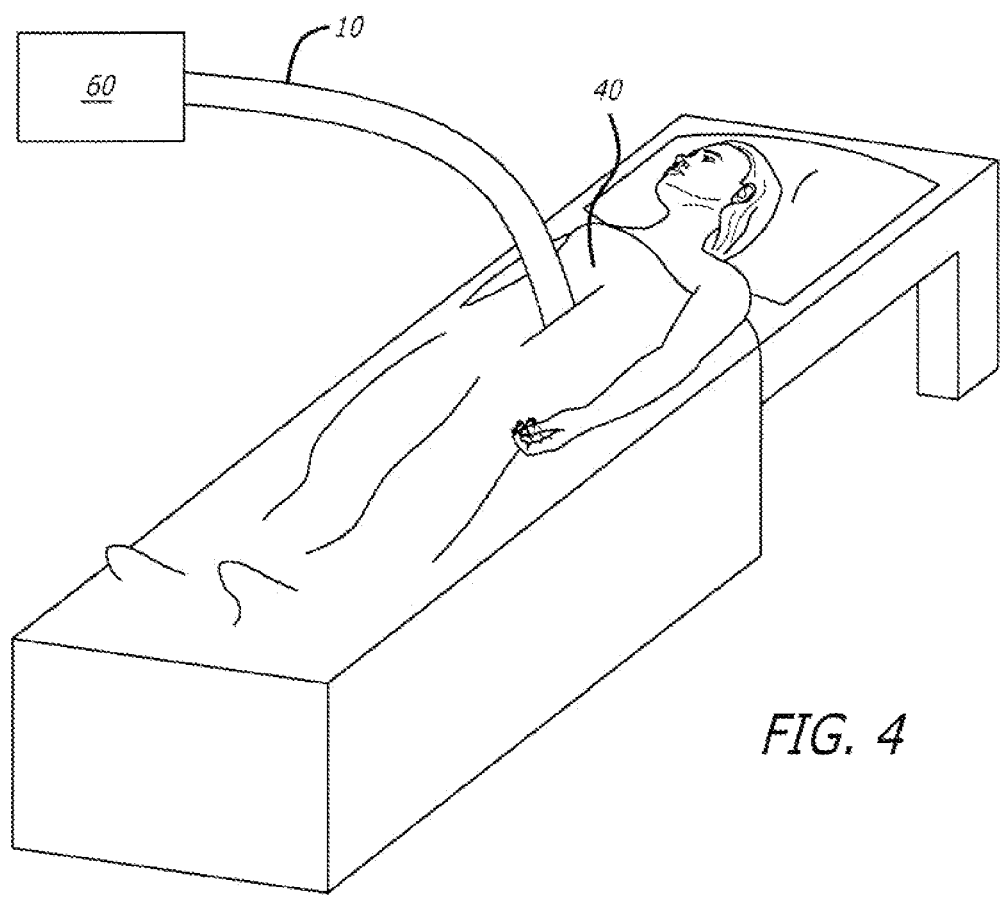
FIG. 4 depicts a schematic diagram of minimally invasive implantation of the interface device 10 into a patient

The inner catheter conductor 120 is adapted to be connected to an energy source (for instance, an energy source contained within machine 60, or operable with machine 60, as shown schematically in FIG. 4). The inner catheter conductor 120 can have any suitable size, shape, length, and dimensions including, diameter and circumference. In one example, the inner catheter conductor 120 can have a diameter or approximately 0.010 inches.

FIG. 4 depicts one exemplary procedure for minimally invasive implantation of the interface device 10 into a patient.

During implantation of the device 10 in the patient, as shown in FIG. 4, she distal portion 40 of the device 10 passes through the chest wall 40 of the patient. In this embodiment, the inner catheter conductor 120 is adapted to be connected electrically to an energy source (e.g., an energy source contained within machine 60, or operable with machine 60).

The interface device 10 is minimally invasive and confers surprising benefits in terms of ease and convenience of implantation in a patient, and removal from a patient. Described herein are representative procedures for achieving minimally invasive implantation of an interface device 10 of the present invention. FIG. 4 is a schematic view showing the minimally invasive device 10 of FIG. 3A protruding through the chest wall 40 of a patient, after the chest wall 40 has been closed. Referring again to FIG. 4, and according to one preferred method of implanting the device 10 to treat a cardiac rhythm disturbance in a patient, the method comprises (i) implanting the minimally invasive device 10 through a chest wall of the patient, such that the device 10 is operable for treating the patient. The proximal portion 20 of the device, including the inner catheter conductor 120, is connected to an energy source (for instance, an energy source contained within machine 60).

FIG. 4 depicts a schematic diagram of minimally invasive implantation of the interface device 10 into a patient. As depicted in FIG. 4, the device 10 protrudes through the chest wall 40 of a patient, after the chest wall 40 has been closed. Although the device 10, in which the leaflet assembly 50 is housed in bundle form (as depicted in FIG. 3A), is shown as extending from the patient to a machine 60, the central portion 30 and distal portion 40 of the device 10 need only extend through the chest wall 40 at which point extension cords (or other suitable wiring) could connect the proximal portion 20, including the inner catheter 100 (which houses the inner catheter conductor 120 and the drug delivery channel 400) to the machine 60. In addition, the machine 60 may comprise an EKG monitor, a defibrillator (i.e., a defibrillating power supply), a defibrillation device, a drug delivery device such as a pump (which may be adapted to administer at least one or more drugs either continuously or as a bolus), and/or a combination of any of two or more of these machines.

In one preferred embodiment, the machine 60 can be used to monitor the patient's heart rate and will provide defibrillation energy through the device 10 to at least one of the atria (as depicted in FIG. 4). Thus, in one preferred embodiment, the machine 60 will contain monitoring equipment for monitoring the patient's heart rate and will provide defibrillation energy, as needed, to the patient's heart through electrical defibrillation wire(s) that are connected electrically to device 10. If atrial fibrillation or other cardiac rhythm disturbance is detected, the machine 60 may transmit defibrillating energy (for example, on the order of 1.0 to 3.0 joules) through one or more of the plurality of leaflets 55 to the atrial surfaces of the patient.

In another embodiment, the machine 60 may also be used to monitor the nature of the atrial rhythm and may be used (for example, via a drug infusion pump connected to drug delivery channel 400) to control and administer additional quantities of an antiarrhythmic and/or anesthetic drug (e.g., procaine, procainamide, amiodarone, lidocaine, and/or combination of one or more other drugs) as needed. The anesthetic drug may, for example, be selected from the group consisting of procaine, lidocaine, a combination of procaine and at least one other anesthetic drug, a combination of lidocaine and at least one other anesthetic drug, and a combination of procaine, lidocaine, and at least one other anesthetic drug.

According to the present invention, one or more drugs or pharmaceutical agents can be administered, for example, either continuously or as a bolus, such that the agents are released through the release site 420 from where the drugs or pharmaceutical agents can diffuse into the atrial surface. In addition to the amount of drug delivered, the present invention provides the physician or other healthcare professional with the ability to easily, reliably, safely and efficiently control the timing, dosing schedule and frequency at which the drug or drugs are administered, the duration over which the drug is administered, and the amount and type of drug administered.

Thus, according to a preferred embodiment, the present invention provides for monitoring the atrial surface for atrial fibrillation or other type of cardiac rhythm disturbance. If atrial fibrillation is detected, the present invention provides electric charge with an appropriate amount of energy to defibrillate the heart; and also delivery of at least one or more drugs to the heart via the one or more drug delivery channels 400 within the inner catheter 100 passing through the chest wall 40 of the patient. At a suitable and appropriate time, the device 10 can be safely, easily and efficiently removed with no discomfort or pain to the patient.

Figure 6A:
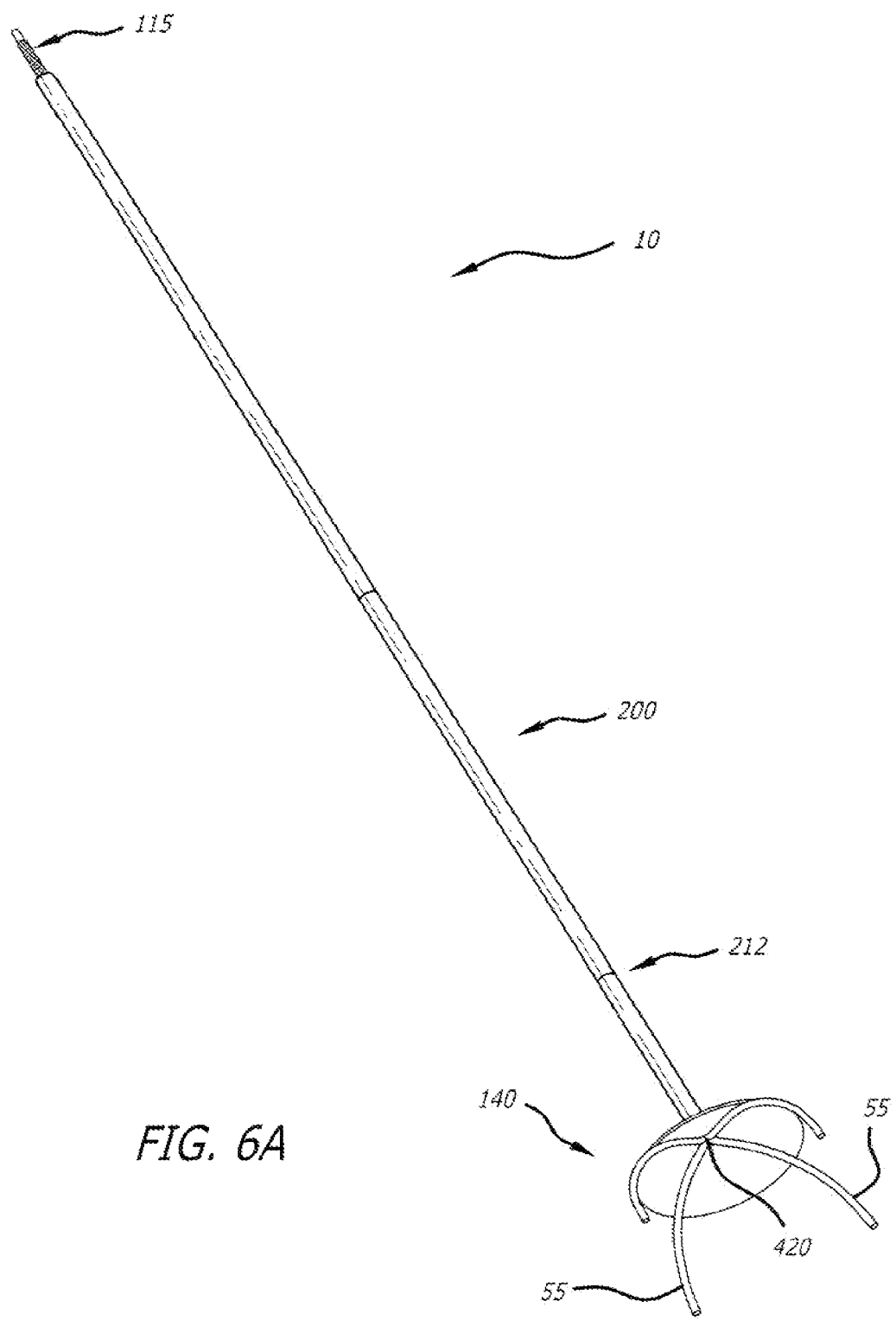
FIGS. 6A and 6B depict another representative embodiment of an interface device 10, wherein the leaflet assembly 50 has been spread out, in preparation for contact with the heart.
Figure 6B:
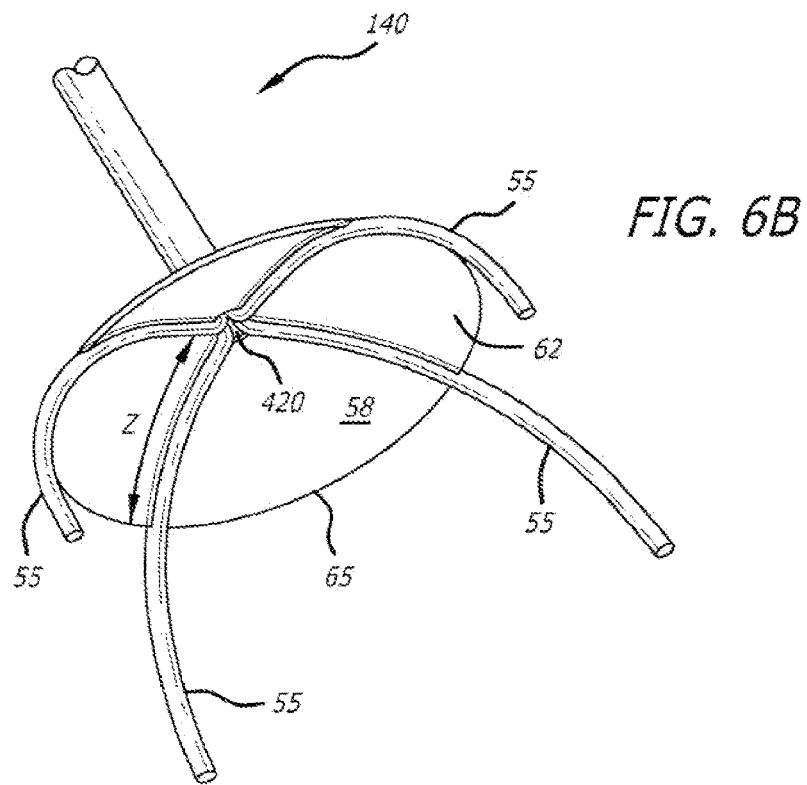

It is preferred that the drug delivery channel 400 extends lengthwise along the entire length from the opening 405 of the proximal portion 20 of the device 10, through the central portion 30 of device 10, and then the drug delivery channel 400 preferably ends at the release site 420 (see, for example, FIGS. 3A, 3B and 6B).

Figure 6C:
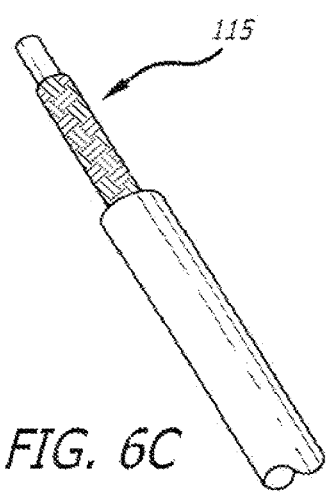
FIGS. 6C and 6D depict an example of a braided shield in accordance with the present invention.
Figure 6D:
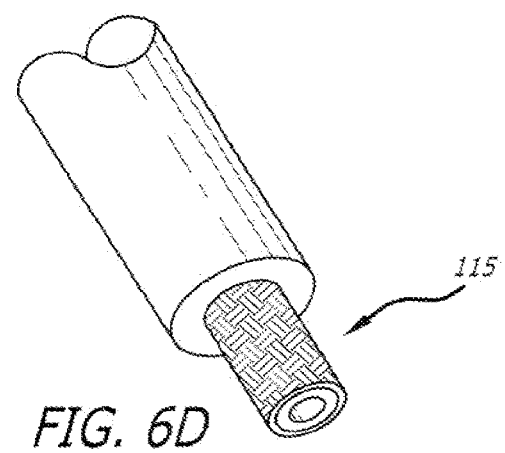

The drug delivery channel 400 is thus essentially a lumen or opening resembling a lumen, opening or inside space of a tubular structure. The length, width and diameter of the drug delivery channel 400 can vary as needed when the device 10 is manufactured. According to one example, the drug delivery channel 400 can be approximately 45 cm in length, and can be manufactured out of one or materials that are compatible with pharmaceutical agents, since the pharmaceutical agents will be delivered through the channel 400. Referring to FIGS. 6C and 6D, as described in further detail herein, the length of the braided shield 115 is similar in length to the length of the drug delivery channel 400.

Pharmaceutical agents exit at the release site 420 for local, targeted delivery to the heart. Upon release from the release site 420, the pharmaceutical agents exit and generally flow underneath the dome 62, and are thus essentially trapped temporarily against the intended cardiac surface which likely potentially increases their effect on the heart.

In one embodiment, the device 10 can be implanted using a video assisted minimally invasive procedure. In one preferred example, a patient will be under general anesthesia and right lung ventilation to be able to deflate left lung. If desired or necessary, a small tube (an "introducer tube", not shown) can be inserted through the chest wall 40. The device 10 (as shown schematically in FIG. 3A) can be threaded through the introducer tube into the patient's left chest cavity, to the bilateral atrial surfaces. The distal end 40 of the device 10 can be fixed and positioned in place by using clips, suture or other suitable attachment means to affix onto the pericardial surface. The device 10 can then be operated for delivering electric charge (or electrical defibrillation energy) and/or local delivery of pharmaceutical agents to the heart.

The device 10 can optionally be connected to one or more pumps, for example one or more micro-pumps (not shown in the figures), which can optionally be used to locally deliver one or more pharmaceutical agents to the heart. Such a pump (e.g. micro-pump) could be similar to a pacer or insulin pump implantation, except that the pump would preferably be programmed wirelessly to regulate local delivery and dosing of one or more pharmaceutical agents to the heart. Preferably, the pump would be connected to the proximal portion 20 of the device 10.

In one embodiment of the invention, a separate device 10 that includes a leaflet assembly 50 containing the plurality of leaflets 55 (e.g., when the leaflets 55 are configured as shown in FIG. 6A) is placed on the atrial surfaces of the right and left atria during a minimally invasive surgical procedure and before the patient's chest is closed. By placing a device 10 on each of the atrial surfaces, the amount of energy needed may be 50% less than that needed for the situation in which one device 10 is placed on the atrial surface of one atrium, and no device is placed on the atrial surface of the other atrium.

Figure 5A:
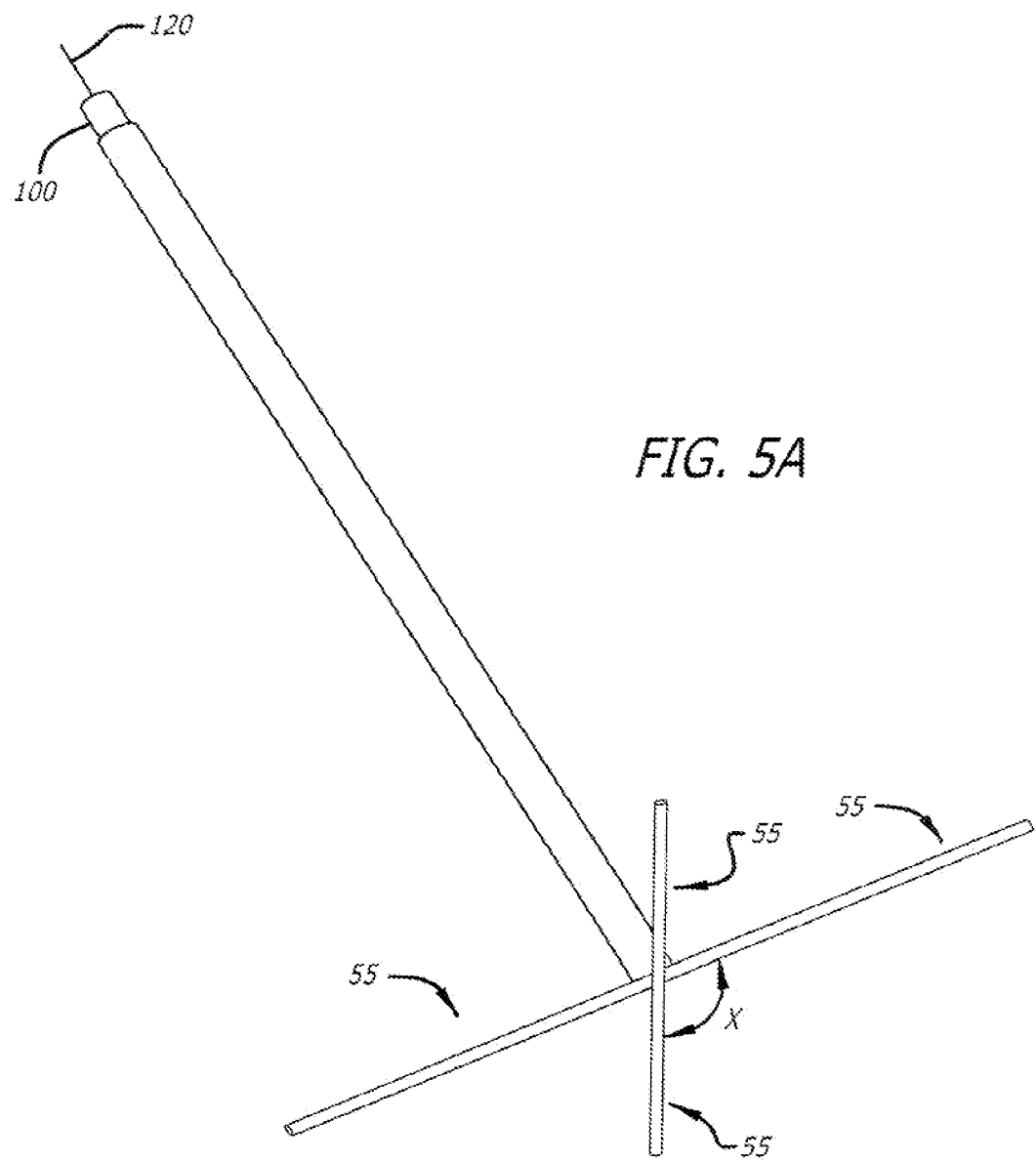
FIGS. 5A and 5B depict one representative embodiment of an interface device 10, after the leaflet assembly 50 has been spread out, in preparation for contact with the heart.
Figure 5B:
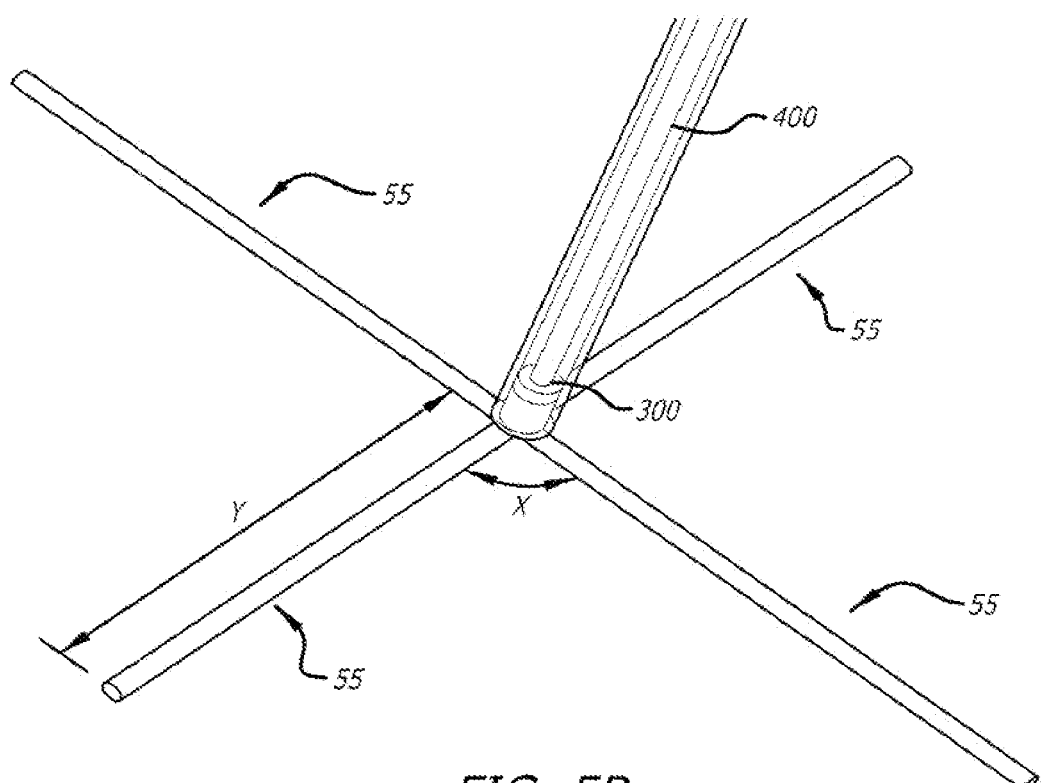

Referring to FIGS. 5A and 5B, another representative embodiment of an interface device 10 is shown. In the sample configuration shown in FIGS. 5A and 5B, the leaflet assembly 50 has been spread out, in preparation for contacting the leaflet assembly 50 with the heart. Even though four leaflets 55 are shown in FIGS. 5A and 5B, this is just one example. It is to be understood that the leaflet assembly 50 can comprise any number of leaflets 55, for example, one, two, three, four, five, six, or more leaflets, or any suitable number of leaflets 55.

The size and length of the leaflets 55 and thus the leaflet assembly 50 and flower-like arrangement 140 can be trimmed or otherwise suitably adjusted to correspond to the size of the atrial surface to which the flower-like arrangement 140 is subsequently placed. Moreover, the leaflet assembly can be constructed such that the angle (designated by "X" in FIG. 5B) between each leaflet 55, as depicted in FIGS. 5A and 5B, can be adjusted as needed or desired. Any suitable technique can be used for adjusting the length of the leaflets 55, during the process of designing the leaflets 55. For example, the leaflets 55 can be trimmed to a certain length. The length of each leaflet 55 (designated by "Y" in FIG. 5B) can be adjusted as needed or desired.

In addition to the other functions of the leaflets 55 as described herein, the leaflets 55 also preferably function as anchors, i.e., such that a healthcare professional can use stitches or other suitable fastening means to attach to the leaflets 55 in order to anchor or secure the flower-like arrangement 140 to the intended heart surface. According to one embodiment, one or more of the leaflets 55 may include one or more slots (within the leaflet 55) which provide a secure and suitable means for stitching the flower-like arrangement 140 to the intended heart surface.

Referring to FIGS. 6A and 6B, another representative embodiment of an interface device 10 is shown. In the configuration shown in FIGS. 6A and 6B, the leaflet assembly 50 has been spread out, in preparation for contacting the leaflet assembly 50 with the heart 15. The position of the leaflets 55 can be easily maneuvered for making contact with the heart.

According to this embodiment of the present invention, again referring to FIGS. 6A and 6B, this leaflet assembly 50 in the spread-out configuration forms a flower-like arrangement 140. The particular example of the device 10 shown in FIG. 6A comprises the inner catheter 100 and outer catheter 200 described herein (as shown in the example in FIG. 3B). The outer catheter 200 also functions essentially as an introducer, i.e., the outer catheter 200 is operable for introducing and guiding the inner catheter 100 to the appropriate location for placement over an atrial surface or other surface of the heart.

In a preferred embodiment of the invention, for forming the "flower-like" arrangement 140, each of the leaflets 55 can be made from a mold process. In one example, each leaflet 55 is preferably made of low durometer (for example, 30A) implant-grade silicone-rubber heavily-doped with silver. It will be understood to those familiar in the art that any embodiments expressed herein do not in any way limit the scope of the present invention. For example, in lieu of silicone or silicone-rubber heavily-doped with silver, the leaflets 55 may also be constructed of material one or more materials that are permeable to certain drugs, thus enabling greater diffusion of the drugs to the heart tissue.

The proximal portion 20 of the device 10 (shown in FIG. 6A) extends outside the patient body wherein any variety of connections can be established for delivery of either or both electrical and/or chemical defibrillation to the heart. During a cardiac surgery, for example an open-heart surgery, each of the plurality of leaflets 55 of the flower-like arrangement 140 are very flexible and each leaflet 55 may be secured to a surface region of the heart via stitching, adhesive, hook, or other means commonly known to those in the art. The inner catheter 100 preferably extends from the heart to outside the patient body. When the minimally invasive implantable device 10 is to be removed, the healthcare provider holds the outer catheter 200, and pulls the inner catheter 100 and thus the flower-like arrangement 140 out of the body, through the outer catheter 200.

During minimally invasive removal of the device 10 from a patient, the geometry, shape and flexibility of the flower-like arrangement 140, enables the healthcare professional to easily fold the plurality of leaflets 55 into a more straight configuration (as shown, for example, in FIG. 13) and thus pull the plurality of leaflets 55 into the distal end 212 of the outer catheter 200. This minimally invasive removal procedure greatly reduces the difficulty of extracting the device 10 through the chest wall 40 and out of the patient, and avoids the problems associated with invasive procedures.

In one embodiment, the distal end 212 of the outer catheter 200 may be flanged, thus increasing its diameter at the distal end 212, and thus facilitating the process of folding and pulling the flower-like arrangement 140 within the outer catheter 200, for easy and convenient removal from the patient.

As further shown in FIGS. 6A and 6B, the plurality of leaflets 55 can be joined and interconnected by a flexible membrane 58. This representative configuration of the membrane 58 effectively forms a dome 62 that joins and interconnects the plurality of leaflets 55. Preferably, the membrane 58 is made of a flexible and elastic material. By adjusting the thickness of the membrane 58, and utilizing a flexible and elastic material for membrane 58, the device 10 reduces or eliminates at least some of the problems associated with conventional attempts at treating cardiac rhythm disturbances, including the use of pads (as described, for instance, in U.S. Pat. No. 6,965,798, the contents of which are incorporated by reference herein in their entirety). Some of the problems associated with pads, as described, for instance, in U.S. Pat. No. 6,965,798, include the inability of conventional pads to deform with the beating of the heart and the related problem of inhibiting successful heart beats.

The membrane 58 is flexible and elastic in nature so that it can change shape as needed, e.g., change shape with the beating of an atrium when the membrane 58 covers an atrium, and in such a manner that the membrane 58 does not interfere with the beating of the atrium. The membrane 58 can be made of one or more suitable materials including, for example, but not limited to, gelatin, silicon, or any combination thereof. The membrane 58 and dome 62 are effective for containing any pharmaceutical agents that exit through the release site 420 for local administration to the heart. In other words, the membrane 58 and dome 62 effectively function to contain the pharmaceutical agents that exit through the release site 420, such that the pharmaceutical agents (upon exit through the release site 420) are localized generally within the vicinity of the heart that is in contact with the plurality of leaflets 55.

Referring again to FIG. 6B, as a result of the area covered by the dome 62 and plurality of leaflets 55, the electric charge applied to the atrium is substantially uniform over the surface area thereof. Further, as the dome 62 and plurality of leaflets 55 are preferably in direct contact with, and substantially cover the atrial surface the atrium, the amount of energy needed to defibrillate the heart will very well be below that which would cause discomfort. Thus, the methods and device according to the present invention preferably (a) increase the success rate of the electric charge applied to the atrium, to achieve the desired clinical result: (b) reduce the amount of energy applied to the heart; and (c) improves upon the patient's overall comfort. These are some of the many novel and unexpected advantages of the present invention.

The dome 62 is preferably circular in shape, or substantially circular in shape, and it can be flexible and also have any suitable size, shape and dimensions. The dome 62 can be configured to have any diameter and circumference as needed or desired. For instance, the dome 62 can have any diameter from about 1.0 centimeters to about five centimeters, preferably about four centimeters in diameter, and more preferably the dome 62 has a diameter of about 3.5 centimeters. The dome 62 can also have any suitable thickness, for example, the thickness of the dome can be from about 0.01 inches to about 0.05 inches, preferably about 0.03 inches, and more preferably about 0.025 inches in thickness. The thickness of the dome 62 can also be substantially uniform throughout the entire dome 62.

Preferably, each of the leaflets 55 extends from about 5 cm to about 8 cm from the release site 420. However, the length of each of the leaflets 55 (and the corresponding conductive elements 520) may be cut, trimmed, or otherwise adjusted at the time of implantation, to correspond to the size of the atrial surface to which the flower-like arrangement 140 will be affixed. In one example, each of the leaflets 55 is about 2.5 centimeters in length, and more preferably about 2.6 centimeters in length.

According to the methods of the present invention, it is also possible to locally anesthetize tissue surrounding the heart with one or more anesthetic agents before the step of providing electrical charge to the atrial surface with a predetermined amount of energy to defibrillate the heart. It is also possible to expose the atrial surface of the heart with one or more antiarrhythmic agents either during or after the step of providing electrical charge to the atrial surface with a predetermined amount of energy to defibrillate the heart.

In one embodiment, the membrane 58 is preferably knitted or woven, so that at least some portion of the drugs released via the release site 420 will readily diffuse along the membrane 58 to the region of the heart that is covered by the flower-like arrangement 140. From the release site 420, the drugs may thus be readily transmitted to a substantial portion of the surface area of the atrium that is covered by the flower-like arrangement 140.

The membrane 58 can be formed such that the outer perimeter 65 of the dome 62 can be located at any distance or length from the release site 420. This distance, i.e., the distance from the release site 420 to the outer perimeter 65, is designated by the letter "Z" in FIG. 6B. Thus, while the plurality of leaflets 55 carry electrical charge to the heart, the pharmaceutical agents (upon exit through the release site 420) provide localized pharmaceutical treatment since the pharmaceutical agents are released directly within the vicinity of the heart (as depicted schematically in FIGS. 1 and 2).

In other embodiments, the underside of the dome 62 may preferably comprise an adhesive applied thereto, to enable the membrane 58 to adhere to an atrial surface. The adhesive may comprise, for example, gelatin, silicon, protein polymers, collagen pellets, and/or thrombin.

In another embodiment, the membrane 58 is bioabsorbable. In this embodiment, the membrane 58 can safely be designed to be bioabsorbed over the time during which the device 10 is implanted. After the membrane 58 has been bioabsorbed, the plurality of leaflets 55 are readily pulled through the outer catheter 200 for removal from the patient at the appropriate time, through the patient's chest wall 40, as determined by a healthcare professional.

The present invention also provides for delivery of electrical charge (e.g., electrical defibrillation) by use of an electrically conductive braided shield 115.

Referring to FIGS. 6C and 6D, in a preferred embodiment, the braided shield 115 effectively surrounds the drug delivery channel 400. The braided shield 115 can be connected by any suitable means to existing electrical delivery systems. Preferably, electrical charge can be transmitted from an external electrical delivery system (e.g., an energy source housed in machine 60) to the braided shield 115 of the device 10. The electrical charge from the energy source is thereby conducted along the braided shield 115 to the plurality of leaflets 55 for delivery of electrical charge to the heart. The braided shield 115 is preferably made of stainless steel, silver, or one or more other conductive materials, or any combination thereof, and thus the braided shield 115 is capable of transferring electrical charge to the leaflet assembly 50 and thus transferring electrical charge to the heart.

When a braided shield 115 is used, electrical charge can thus be transferred from the braided shield 115 so the plurality of leaflets 55 and thus to the heart, whereby the electric charge is carried preferentially through the paths of least resistance. In preferred embodiments, the paths of least resistance are those with the highest concentration of electrically conductive substance (for instance, silver). Thus, it is preferred that the leaflets 55 are made of low durometer (for example, 30A) implant-grade silicone-rubber heavily-doped with silver.

The number of leaflets 55 can vary as needed or desired, for example, to more or less than four, or distributed asymmetrically. The leaflets 55 of the present embodiment represent a distribution in the electrical charge delivery, and additionally facilitate the true path of least resistance, through increased statistical chance of being ideally near to regions of the cardiac surface with the lowest electrical resistance. The leaflets 55 can also be trimmed (adjusted in length and size) in real-time as required to conform to individual patient heart surfaces.

Figure 7A:
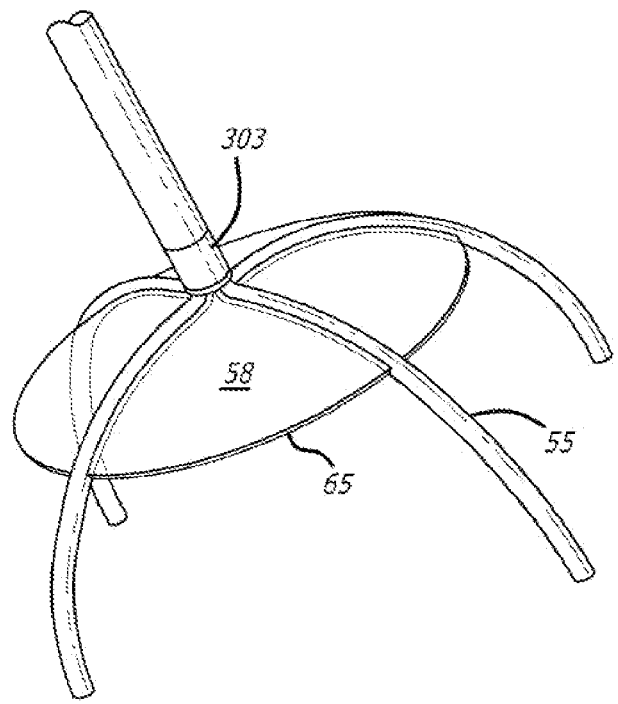
FIGS. 7A and 7B depict an expanded view of one end of an interface device 10, wherein the leaflet assembly 50 has been spread out, in preparation for contact with the heart.
Figure 7B:
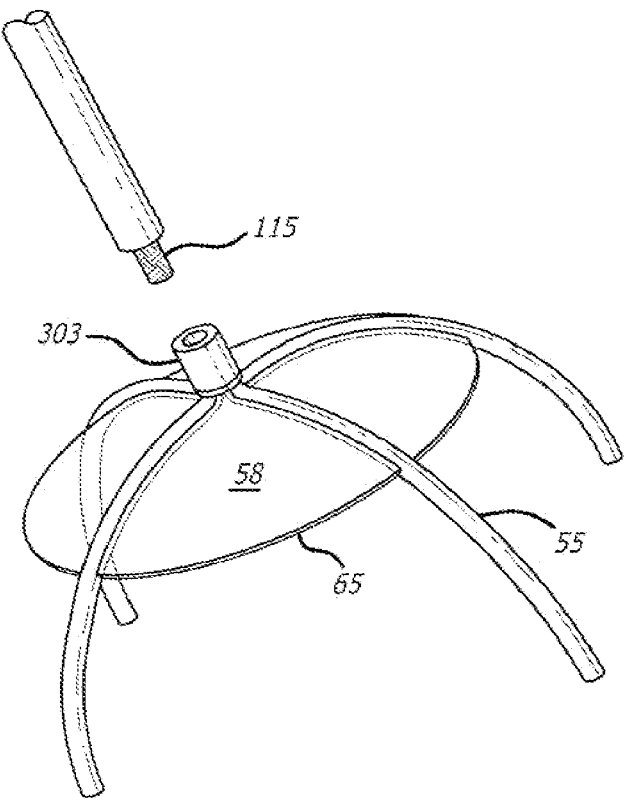

Referring to FIGS. 7A and 7B, an expanded view of the distal portion 40 of one embodiment of an interface device 10 is shown. FIG. 7A depicts an inner catheter 100 connected to the flower-like arrangement 140. In the example shown, the flower-like arrangement 140 comprises a plurality of leaflets 55 that are interconnected by a membrane 58 forming a dome 62. A joint 303 can be used to attach the flower-like arrangement 140 to the inner catheter 100.

Any suitable process can be employed for connecting the inner catheter 100 to the flower-like arrangement 140. One exemplary process involves the use of injection molding to mold a joint 303 directly onto a braided shield 115. The joint 303 is directly connected to each of the plurality of leaflets 55. Thus, electrical conductivity from one or more conductors in the inner catheter (including, for example, the inner catheter conductor 120 shown and described in FIG. 3A, and FIGS. 11C, 11D and 11E) passes very efficiently from the inner catheter 100 to the plurality of leaflets 55. FIG. 7A shows the distal portion 40 of the device 10 after the joint 303 has been overmolded directly onto the braided shield 115. This novel configuration of the device 10 achieves surprising and unexpected efficiency with regard to delivery of electrical conductivity to the leaflets 55 and thus efficient electrical defibrillation of the heart, for convenience. FIG. 7B shows the same configuration before the joint 303 has been overmolded directly onto the braided shield 115.

Figure 8A:
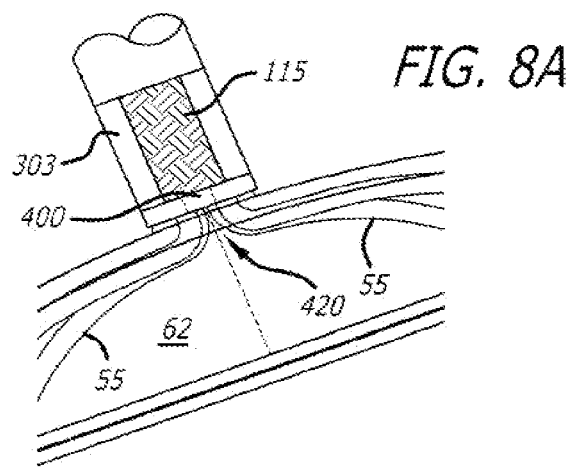
FIGS. 8A, 8B and 8C depict a further expanded view of one end of an interface device 10, wherein the leaflet assembly 50 has been spread out, in preparation for contact with the heart, and which also depicts a release site where pharmaceutical agents exit for contact with the heart.
Figure 8B:
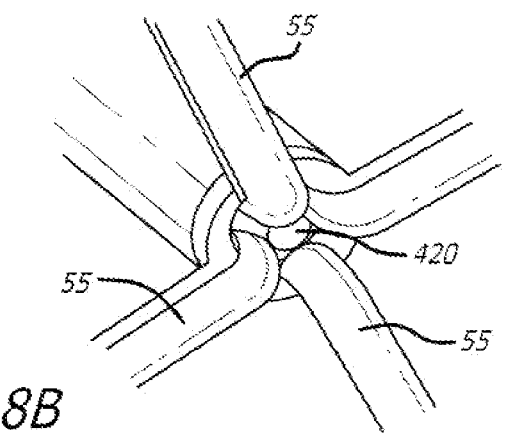
Figure 8C:
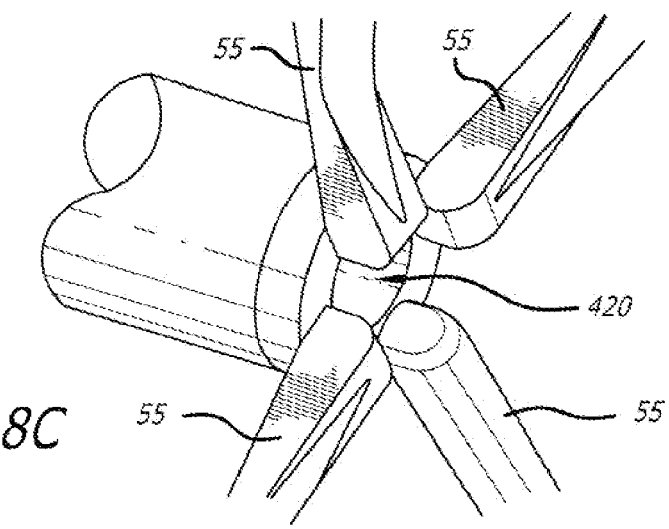

FIGS. 8A, 8B and 8C depict expanded views of the release site 420, as shown and described above with reference to FIG. 6B.

In this configuration, the leaflet assembly 50 is spread out, in preparation for contact with the heart, as depicted in FIGS. 6A and 6B. Referring again to FIGS. 8A, 8B and 8C, the release site 420 functions as an opening where one or more pharmaceutical agents exit the drug delivery channel 400 for contact with the heart. It is to be understood that the concentration, amount, volume, speed and other parameters of delivery and release of the one or more pharmaceutical agents through the drug delivery channel 400 can be adjusted or modulated as needed or desired, depending on the needs of the patient being treated, and based on the professional judgment of healthcare professionals.

As described herein, the dome 62 is effective for containing any pharmaceutical agents that exit through the release site 420 for local administration to the heart. In other words, the membrane 58 and dome 62 effectively function to contain the pharmaceutical agents that exit through the release site 420, such that the pharmaceutical agents (upon exit through the release site 420) are localized generally within the vicinity of the heart that is in contact with the plurality of leaflets 55.

Referring to FIG. 9, one representative embodiment of a connecting portion 300 is shown. Although depicted as generally round and circular in shape along the outside, it is to be understood that the connecting portion 300 can have any suitable shape and size. In the representative embodiment shown in FIG. 9, the connecting portion 300 has a plurality of openings 290. As discussed in further detail herein, with reference to FIGS. 11A-11E, each leaflet 55 can be inserted within a corresponding opening 290, during the construction of device 10. The connecting portion 300 also includes slot 295. As discussed in further detail herein, with reference to FIGS. 11A-11E, the inner catheter conductor 120 can be inserted into slot 295. When the inner catheter conductor 120 is inserted into slot 295, this completes an electrical circuit that distributes substantially even or substantially uniform charge among the plurality of leaflets 55. Connecting portion 300 is preferably highly conductive, and can be made entirely of silver, or include a substantial or significant percentage of silver, or other suitable alloy, metal, alloy metal, or any suitable combination of one or more metals and/or alloys. In certain embodiments, connecting portion 300 can be covered with an electrically non-conductive coating, e.g., during an injection molding manufacturing process.

Figure 10B:
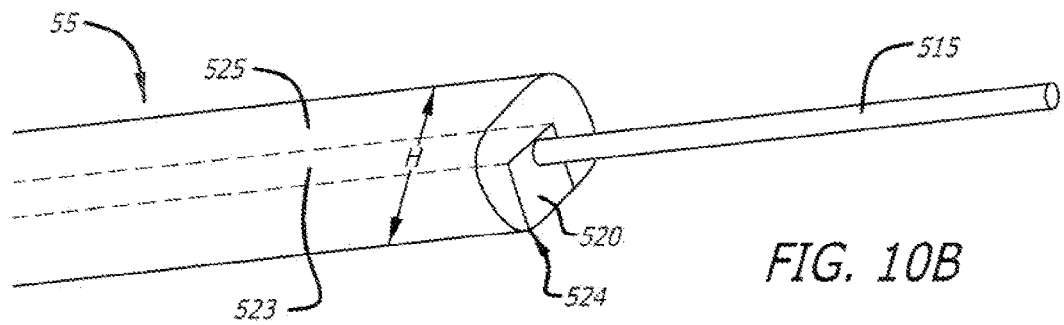

Referring to FIGS. 10A-10B, one representative embodiment of a leaflet 55 is shown. In the preferred embodiment shown, the leaflet 55 comprises one or more conductive elements 520 (as an example, only one conductive element 520 is shown in FIGS. 10A-10B), and one or more electrically conductive wires 515 that are attached to, or inserted within, each conductive element 520. The conductive element 520 and conductive wire 515 are adapted to provide suitable defibrillation energy, or electric charge, to the atrial surface of the patient, or to one or more other surfaces of the patient's heart as needed or indicated by the healthcare professional.

The conductive element 520 can be made of and comprise, one or more suitably conductive elements, metals and/or alloys. For example, in one embodiment, the conductive element 520 can be made using low durometer (e.g., 30A shore) implant-grade silicone robber heavily-doped with silver for optimizing electrical conductivity. The conductive element 520 can be doped with one or more other metals, or combination of metals, depending on the electrical conductivity desired. The conductive element 520 carries electric charge down the entire leaflet 55.

It is preferred that one or more electrically conductive wires 515 are attached to, molded upon, inserted within, or otherwise connected to each conductive element 520. The electrically conductive wire 515 can be made of any suitable conductive element, for instance, copper to form a solid core copper wire. The electrically conductive wire 515 can also be doped with one or more other metals, or combination of metals, to enhance electrical conductivity, for example, wire 515 can be doped with silver for optimizing electrical conductivity. The conductive wire 515 can have any suitable length, size, diameter and other dimensions. For instance, the conductive wire 515 can have a diameter of approximately 0.010 inches.

The conductive element 520 and conductive wire 515 can be manufactured out of any other suitable conductive element, metal, alloy, or combination of one or more conductive elements, metals and/or alloys. The conductive element 520 and conductive wire 515 can be manufactured by any suitable manufacturing process, for instance, an injection molding process.

The size, shape and dimensions of the representative embodiment shown in FIGS. 10A-10B are for exemplary purposes only. The scope of the invention is not limited to the size, shape and dimensions of the representative embodiment shown in FIGS. 10A-10B. For instance, the height (represented by "H" in FIG. 10B) of the leaflet 55 can be anywhere from approximately 0.010 inches to approximately 0.10 inches, and preferably the height "H" of the leaflet 55 is from approximately 0.050 inches to approximately 0.070 inches, and more preferably the height "H" of the leaflet 55 is approximately 0.065 inches.

Referring again to FIGS. 10A-10B, to insulate the tissue surrounding the heart from the energy carried in the leaflets 55 (and correspondingly to ensure that more of the energy is directed to the atrial surface to which the flower-like arrangement 140 and leaflet assembly 50 is adhered), the outer portions of each of the leaflets 55 are preferably covered with a non-electrically conductive (insulator) material 525. The outer portion of each leaflet 55 is preferably covered with a non-electrically conductive (insulator) material 525 that has not been doped. The non-electrically conductive (insulator) material 525 can be formed using any suitable manufacturing process, such as for instance an injection over-molding process. The material 525 can thus be injection molded directly over the conductive element 520.

The non-electrically conductive (insulator) material 525 is preferably clear or substantially clear, and can be made of one or more suitable non-electrically conductive (insulator) material or combination of materials. It is to be understood that any suitable non-electrically conductive (insulator) material or combination of materials can be used in accordance with the present invention.

Referring again to FIGS. 10A-10B, one exemplary process for manufacturing a leaflet 55 is described herein. According to this one exemplary process, a wire 515 (as further described herein) is placed in a mold used in an injection molding process. Then, a suitable injection molding process is used to deposit the conductive element 520

(for example, made of silver-doped, implant grade silicone-rubber) by injection molding over the wire 515. Referring particularly to FIG. 10B, the next step in this exemplary manufacturing process is to deposit the non-electrically conductive (insulator) material 525 (preferably a substantially clear material 525) over the upper portion or top portion 523 of the conductive element 520. As shown in FIG. 10B, this exemplary process can thus be used to create a leaflet 55, in which the bottom portion 524 of the conductive element 520 remains exposed at the bottom (i.e., the bottom portion 524 is not covered by the material 525). In this manner, the leaflet 55 is very effective for safely and efficiently transmitting electrical charge (electric defibrillation energy) to the heart surface that is in contact with the leaflet 55.

FIGS. 11A through 11E depict a series of diagrams that illustrate one representative process for manufacture of a distal portion 40 of a device 10.

Referring to FIG. 11A, one example of a connecting portion 300 is shown, which comprises a plurality of openings 290 and a slot 295. As shown, a wire 515 from each separate corresponding leaflet 55 is inserted and positioned within a corresponding opening 290 of the connecting portion 300. A soldering process may be used to fix the placement of each wire 515 into the corresponding opening 290 of the connecting portion 300. The separate placement of each of the wires 515 is preferred in order that each of the wires 515 remains electrically insulated with respect to each other.

The features of slot 295 will be described in further detail herein, including the schematic shown in FIG. 11C. The connecting portion 300 also comprises at least one drug delivery opening 408, as shown in FIG. 11A. As shown and described further herein, referring to FIGS. 11C, 11D and 11E, the device 10 is preferably designed such that one or more drugs that pass through the drug delivery channel 400 are delivered to the drug delivery opening 408. Upon delivery to the drug delivery opening 408, the one or more drugs are, in turn, delivered to the heart surface via the release site 420 (see, for example, FIG. 6B). Although only one drug delivery opening 408 is shown in FIG. 11A, it is to be understood that the device 10 of the present invention can be manufactured to have a plurality of drug delivery channels 400 and corresponding drug delivery openings 408.

It is also to be understood that, in other embodiments, although not illustrated in the figures, connecting portion 300 may include either more or fewer number of openings 290 and/or slots 295.

Referring to FIG. 11B, this is a depiction of the same device shown and described for FIG. 11A, except that the device shown in FIG. 11B depicts the device after soldering has been used to position each of the wires 515 in place, and after the wires 515 have been trimmed in length.

Referring to FIG. 11C, and as further described herein, the inner catheter conductor 120 is electrically connected to electrical defibrillation wiring that in turn is connected to an external energy source, for example, an energy source contained within machine 60. Sensing and monitoring equipment, for example, equipment contained within machine 60, may be used to sense the patient's cardiac EKG wave and thereby detect a cardiac rhythm disturbance, for example an atrial fibrillation.

As shown schematically in FIG. 11C, when the inner catheter conductor 120 is inserted and mounted within the slot 295 in the connecting portion 300, the inner catheter conductor 120 therefore completes an electric circuit which distributes substantially uniform electric charge among each of the plurality of leaflets 55. Thus, electrical defibrillation (for instance, one or more of a series of electric shocks) may be administered from a biphasic wave delivery system (or other source of electric charge or electrical defibrillation) to the atrial surface via the electric circuit completed by the inner catheter conductor 120. In other embodiments, the present invention provides for asymmetric delivery of electrical charge to different heart chambers, e.g., one device 10 delivers a certain amount of electrical charge to one heart chamber, and another device 10 delivers a different amount of electrical defibrillation to another heart chamber.

Figure 11E:
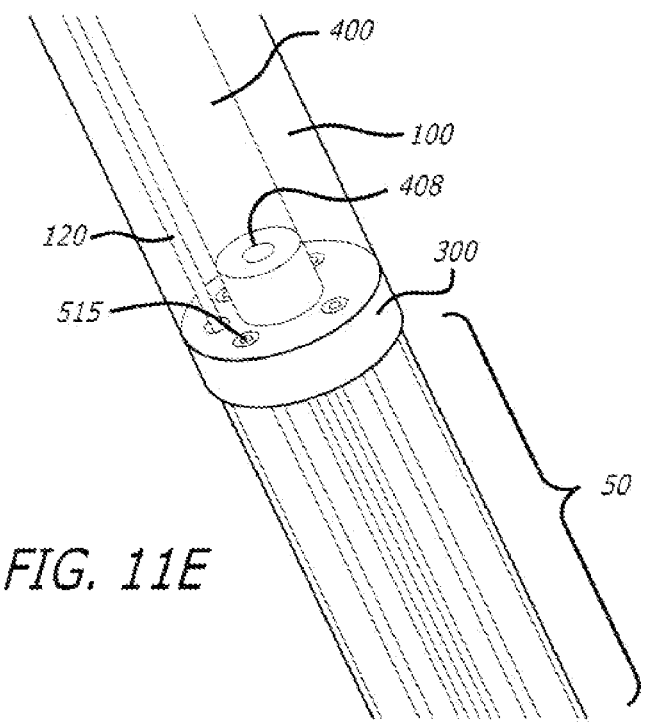

Referring again to FIG. 11C, an adhesive can optionally be applied to the outside of the upper stem 412 of the connecting portion 300 as shown. This optional adhesive can be used, such that when the inner catheter 100 is positioned in place over the connecting portion 300, the adhesive seals in place the inner catheter 100 and the connecting portion 300. The same configuration in FIG. 11C is shown from a different perspective in FIG. 11D. FIG. 11E also shows the same configuration, after the inner catheter 100 has been positioned and sealed in place over the connecting portion 300. Just for illustration purposes, and to make it simpler to view the inner catheter conductor 120, the drug delivery channel 400, and the drug delivery opening 408, FIG. 11E shows a transparent view of the inner catheter 100. As described herein, in preferred embodiments, the inner catheter conductor 120 can preferably be made of copper or another conductive metal, or any combination of conductive metals. FIG. 11F shows a configuration after the inner catheter conductor 120 and the plurality of electrically conductive wires 515 have been secured in place, for example, by a soldering process.

Figure 12:
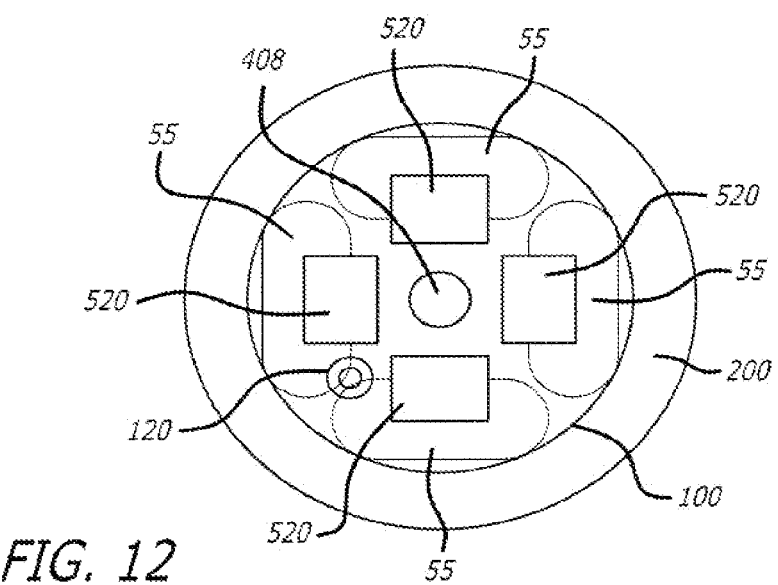
FIG. 12 depicts one representative cross-sectional view of a distal portion 40 of an interface device 10.

FIG. 12 depicts one representative cross-sectional view of a distal portion 40 of an interface device 10. This cross-sectional view shows the plurality of conductive elements 520 of each corresponding leaflet 55, the inner catheter conductor 120, and the drug delivery opening 408, within the inner catheter 100. FIG. 12 also shows the outer catheter 200 in cross-sectional view.

Figure 13:
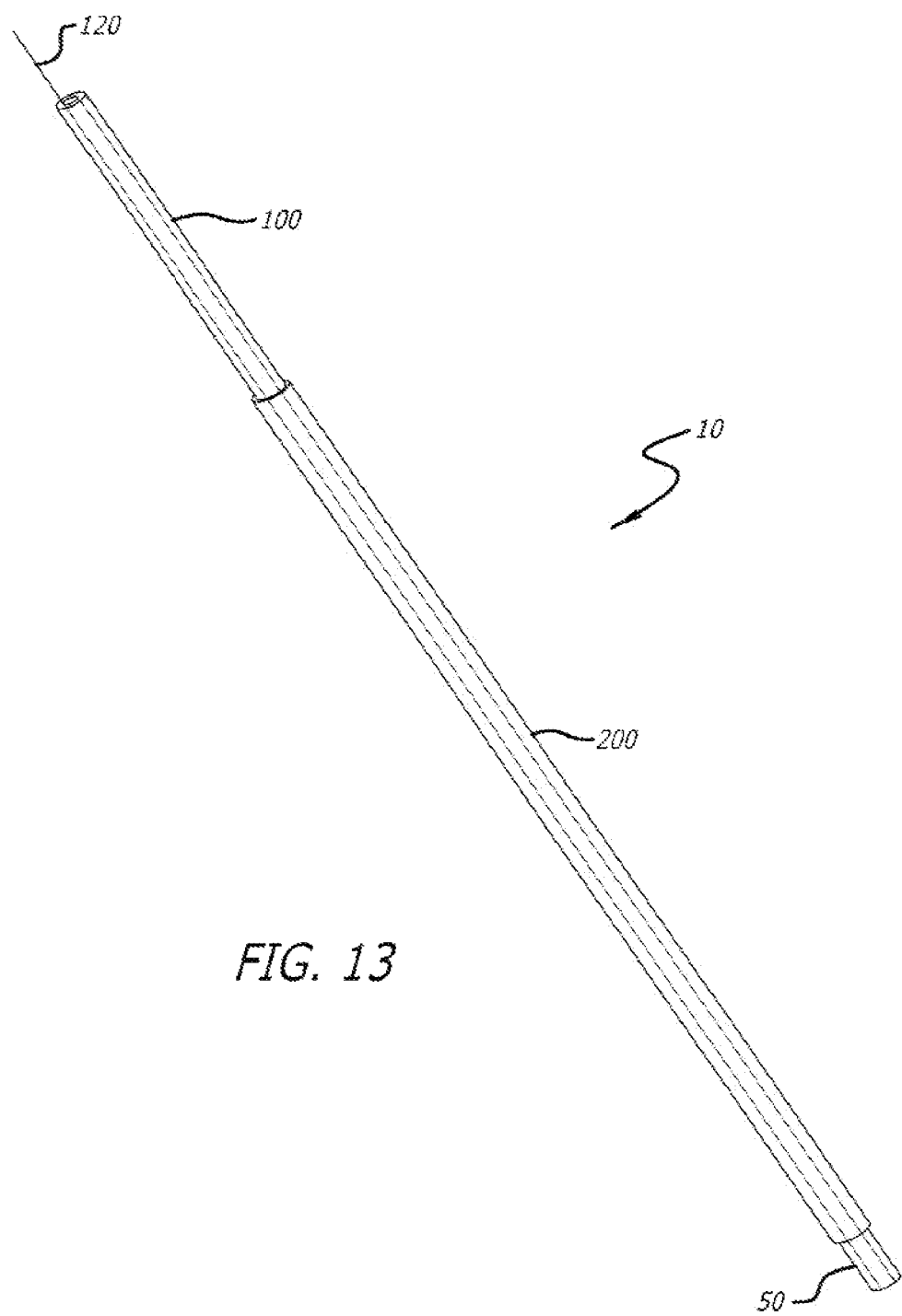
FIG. 13 depicts one representative embodiment of an interface device 10, upon removal from a patient, wherein the inner catheter 100 has been pulled through the outer catheter 200, and further wherein the plurality of leaflets are also pulled through and taken up inside the outer catheter 200.

Referring to FIG. 13, and also FIG. 4, after the risk of atrial fibrillation or other cardiac rhythm disturbance has been alleviated by the present invention, the one or more devices 10 will need to be removed from the patient. Because of the case and minimally invasive nature of the devices of the present invention, which prevent discomfort to the patient, the device 10 is preferably removable without having to reopen the patient's chest wall 40. Referring again to FIG. 13, in a first embodiment of a method for easily removing the device 10 from a patient, the inner catheter 100 (with the inner catheter conductor 120) is easily pulled along with the leaflet assembly 50 through the outer catheter 200. Accordingly, in this manner, the device 10 can easily, safely and efficiently be removed from the patient by pulling the device 10 through the patient's chest wall 40. If more than one device 10 is used in treating the patient, the additional devices 10 may be removed in a similar manner.

Referring again to FIG. 13, upon removal from a patient, the inner catheter 100 has been pulled through the outer catheter 200, and the leaflet assembly 50 has also been pulled through and taken up inside the outer catheter 200. Referring to FIG. 13, the device 10 can thus be easily and safely removed from the patient by simply pulling the inner catheter 100 and leaflet assembly 50 through the outer catheter 200, and pulling the device 10 through the chest wall and out of the patient.

Figure 14A:
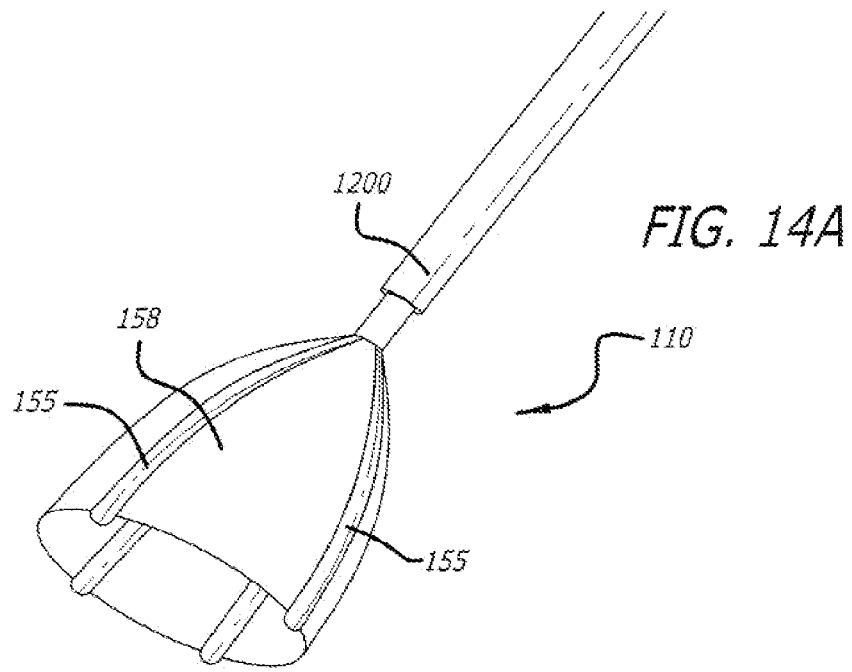
FIGS. 14A-14B depict a representative embodiment of an interface device 110, comprising a plurality of leaflets interconnected by a flexible membrane.
Figure 14B:
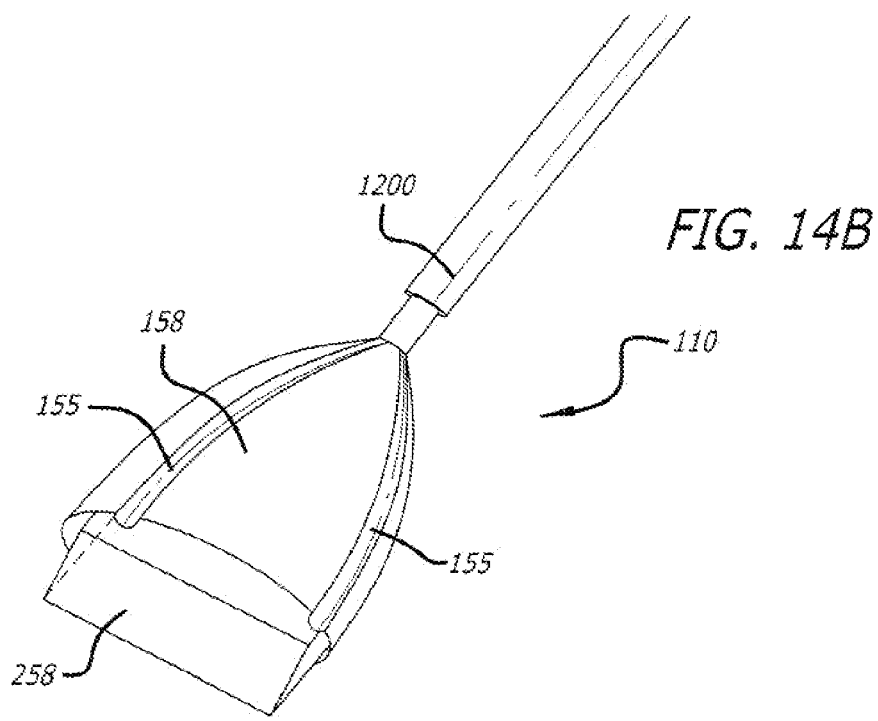

FIGS. 14A-14B depict one representative embodiment of an interface device 110, comprising a plurality of leaflets 155 interconnected by a flexible and elastic membrane 158. The device 110 functions in very much the same manner as the device 10 described herein, in terms of providing both electrical defibrillation (via the plurality of leaflets 155) and also delivery of pharmaceutical agents. The leaflets 155 are preferably placed and distributed (with respect to all the other leaflets 155) for optimal alignment and to achieve optimal clinical effects, based on the geometry, size and shape of the intended cardiac site (e.g., left atrium or right atrium) where electrical and/or chemical defibrillation will be administered. The flexible membrane 158 helps in targeting the drugs or pharmaceutical agents that are locally delivered to the heart.

An outer catheter 1200 of the device 110 is also shown, which functions like the outer catheter 200 of device 10. As shown in FIG. 14A, this representative embodiment of the device 110 forms an elliptical or bell-shaped configuration. Similar to the leaflets 55 described in further detail herein, the leaflets 155 function to provide electrical defibrillation (for example, by delivery of suitable electric charge) to a heart surface, e.g., an atrial surface. The device 110 can be placed over the right atrium, particularly over an anatomical area of the right atrium that resembles in shape a tongue-shaped portion of the right atrium.

In other configurations (not shown in the figures), the device 110 can be designed such that the device 110 includes the flexible and elastic membrane 158, however without any leaflets 155, if it is only desired to deliver one or more pharmaceutical agents, but without delivery of electrical defibrillation, to a heart surface.

FIG. 14B depicts another configuration of the device 110, wherein the device 110 additionally includes a flexible sheet 258, in addition to the flexible membrane 158. The flexible and elastic sheet 258 can be positioned in place over the surface of a heart chamber, for example, over an atrial surface, to further provide for local, targeted delivery of one or more pharmaceutical agents. The bell-shaped or elliptical-shaped portion of the device 110 (as shown in FIGS. 14A-14B) ideally fits as a "glove" when it is placed over the tongue-shaped region of the right atrium, and whereupon the flexible and elastic sheet 258 constricts about the tongue-shaped appendage of the right atrium.

Figure 15A:
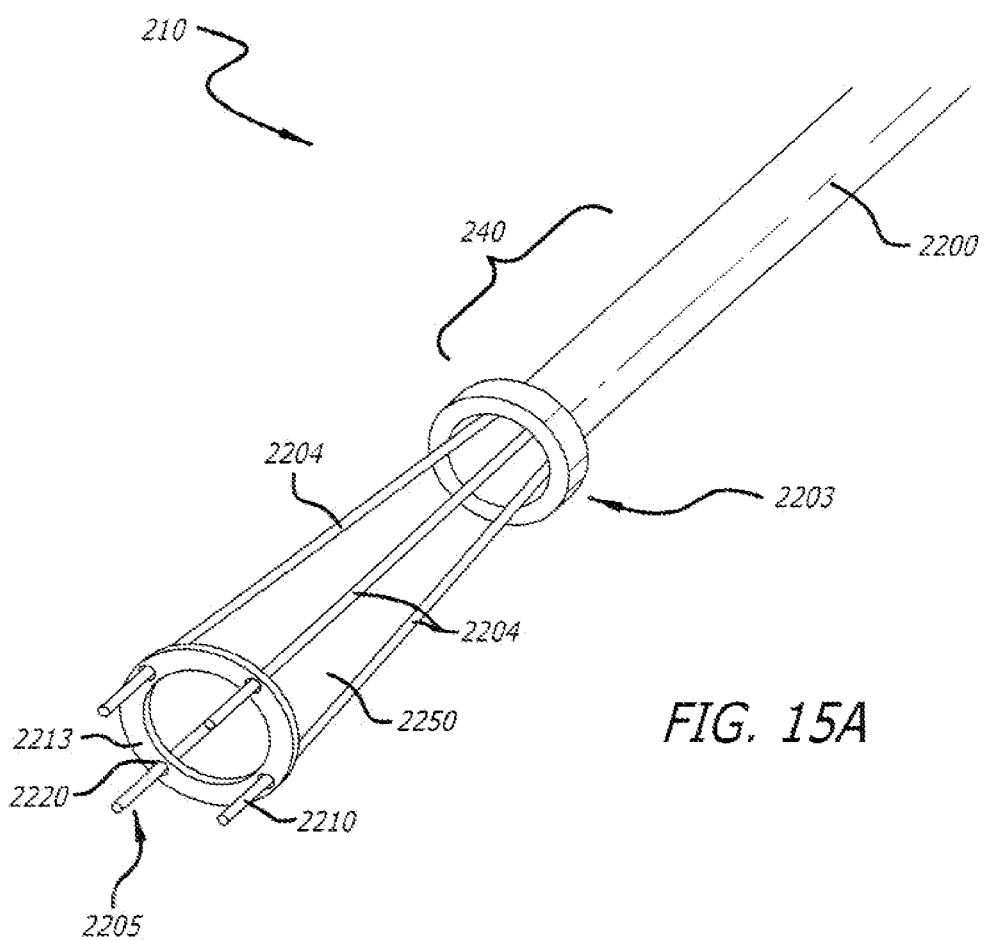
FIGS. 15A-15C depict representative embodiments of an interface device 210, comprising a plurality of bi-metallic strips.

Referring to FIG. 15A, a representative embodiment of an interface device 210 is shown, comprising a catheter 2200 and a distal assembly 2250. The distal assembly 2250 can be made of any suitable flexible or elastic material or combination of materials that inter-connects the plurality of bi-metallic strips 2204.

In the embodiment shown in FIG. 15A, an upper ring 2203 is attached at a distal end 240 of the device 210. The temperature of the upper ring 2203 can be modified either by means of thermoelectric, liquid and/or any other means of convenient temperature control. The ring 2203 preferably contains one or more, and preferably a plurality, of bi-metallic strips 2204 extending in a general orientation as shown in FIG. 15A. Each of the bi-metallic strips 2204 extends and protrudes slightly through a slot 2210 in a distal ring 2213.

The bi-metallic strips 2204 can be utilized to provide electrical defibrillation to the heart. In other configurations (not shown in the figures), the device 210 can also be designed such that the distal assembly 2250 does not include any bi-metallic strips 2204. Such a configuration can be utilized (i.e., if there are no strips 2204) if it is desired to deliver one or more pharmaceutical agents, but without delivery of electrical defibrillation, to a heart surface. In such an embodiment, the device 210 would include the rings 2203 and 2213, and the distal assembly 2250 oriented in a generally bell-shaped configuration (as depicted in FIG. 15A), except without any strips 2204.

In other embodiments, one or more of the rings 2203 and 2213 can also be manufactured such that they are thicker portions of the material itself; for example, e.g. one or more of the rings 2203 and 2213 can be formed of injection molded material. It is to be understood that any suitable material or combination of materials can be used to make the rings 2203 and 2213, bi-metallic strips 2204, and other components of the devices described herein, in accordance with the present invention.

Referring again to FIG. 15A, in this embodiment, the upper ring 2203 also contains one non-bi-metallic strip 2205 which protrudes through a singular bottom slot 2220 in the distal ring 2213. This embodiment of the invention provides for minimally invasive placement of the device 210 over the surface of a heart chamber, i.e., over an atrial surface.

A preferred, representative method of utilizing the device 210 is herein described. A healthcare professional can insert the device 210 in a minimally invasive manner such that the distal assembly 2250 substantially opens or expands. Subsequent cooling of the bi-metallic strips 2204 substantially closes the distal assembly 2250 about the intended heart surface. The device 210 can include any suitable means, and/or be connected to any suitable means, for heating and cooling the bi-metallic strips 2204. Such cooling and/or heating means will preferably be contained within the device 210, and will not pose any safety concern to the patient. Nor will the cooling and/or heating means cause any discomfort, or any other distraction, injury, or any other cause for concern to the patient or the healthcare professional.

In one aspect, heating the bi-metallic strips 2204 substantially opens or expands the distal assembly 2250. Cooling the bi-metallic strips 2204 substantially closes the distal assembly 2250 about the intended heart surface.

In another aspect, the bi-metallic strips 2204 may be formed in a generally open state, whereupon application of cold temperatures closes the distal assembly 2250. The strips 2204 can optionally be removed at this time, i.e., after application of cold temperatures closes the distal assembly 2250 about the intended heart surface. In another aspect, the bi-metallic strips 2204 may be formed in a base state such that application of cold or hot temperatures opens and closes the distal assembly 2250 as needed or desired.

Figure 15B:
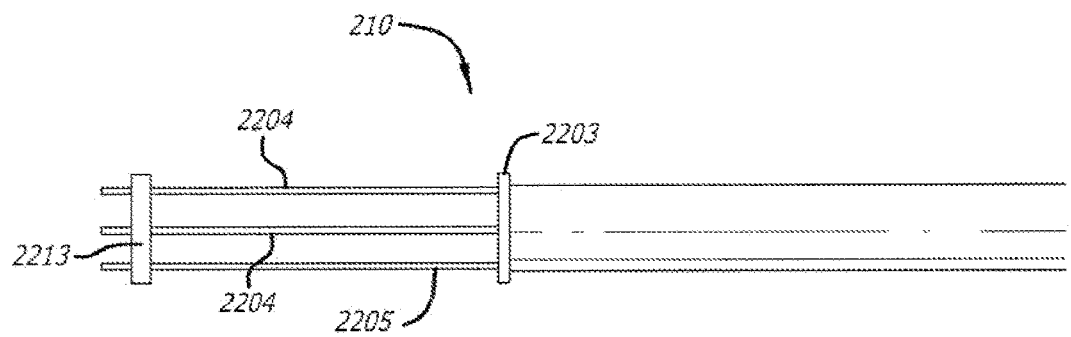

Referring to FIG. 15B, a side-view of the device 210 is depicted schematically, before heat has been applied to the plurality of bi-metallic strips 2204. The non-bi-metallic strip 2205 is also shown, i.e., before heat is applied. As described elsewhere herein, the device 210 can include any suitable means, and/or be connected to any suitable means, for heating and cooling the bi-metallic strips 2204. Such cooling and/or heating means will preferably be contained within the device 210, and will not pose any safety concern to the patient. Nor will the cooling and/or heating means cause any discomfort, or any other distraction, injury, or any other cause for concern to the patient or the healthcare professional.

As shown in FIG. 15B, in the absence of applied heat (or before heat is applied), the bi-metallic strips 2204 are generally straight in then orientation. The distal ring 2213 is in a generally relaxed state before heat is applied.

Figure 15C:
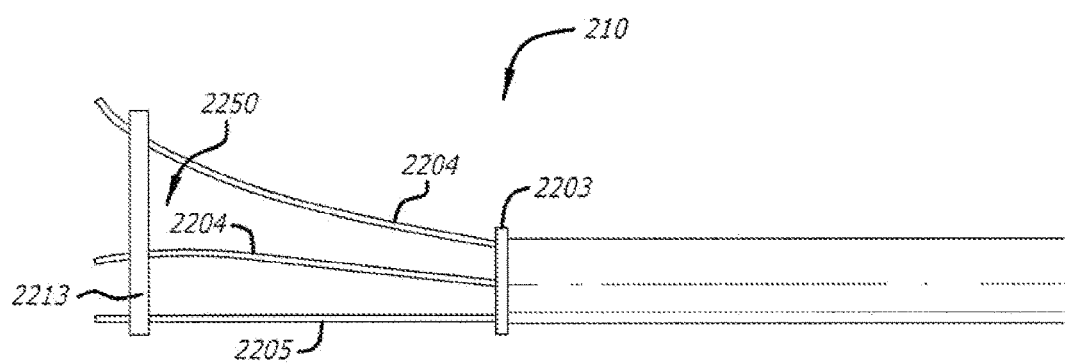

Referring to FIG. 15C, after heat is applied, there is expansion of the bi-metallic strips 2204. Heating the bi-metallic strips 2204 substantially opens or expands the distal assembly 2250, as shown in FIG. 15C. The distal assembly 2250 is shown opened and dilated after heat has been applied.

It is to be understood that any suitable temperature or range of temperatures can be used in accordance with the present invention, e.g., for heating the bi-metallic strips 2204. It is to be understood that suitable temperatures preferably include temperatures that will not impair or damage the tissue of the patient, and which can readily be determined without any undue experimentation (see, e.g., PACE 2003; 26:1379-1385, the contents of which are incorporated herein in its entirety). It is also possible, according to the present invention, if determined as necessary or required by a healthcare professional, to use a slightly higher temperature (e.g., for heating the bi-metallic strips 2204) for a brief or short period of time, including for instance a slightly higher temperature that causes no damage or very minimal tissue damage.

In a preferred embodiment, the device 210 preferably includes one or more components (not shown) that are highly thermally conductive. Thus, when heat is applied to the thermally conductive components, the heat is conducted and transmitted to the bi-metallic strips 2204, and the device 210 is thus operable for efficiently adjusting and controlling the thermal expansion of the strips 2204. Cooling the bi-metallic strips 2204 substantially closes the distal assembly 2250 about the intended heart surface. As shown in FIGS. 15B and 15C, heating does not affect the non-bi-metallic strip 2205. Thus, with or without applied heat or cooling, the non-bi-metallic strip 2205 remains generally straight in its orientation.

As described in further detail herein, similar to the device 10, the device 210 is also operable for providing local, targeted delivery of one or more pharmaceutical agents to the intended treatment site (e.g., an atrial surface). The bell-shaped configuration of the distal assembly 2250 helps to maintain the one or more pharmaceutical agents at the intended treatment site (e.g., an atrial surface).

Figure 16A:
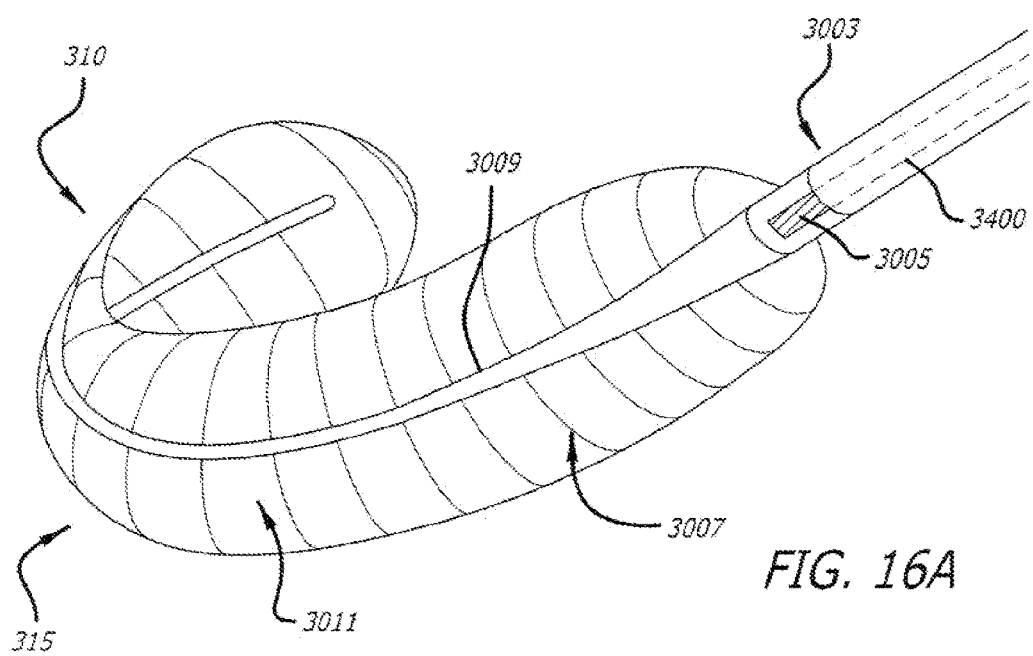
FIGS. 16A and 16B depict one representative embodiment of an interface device 310.
Figure 16B:
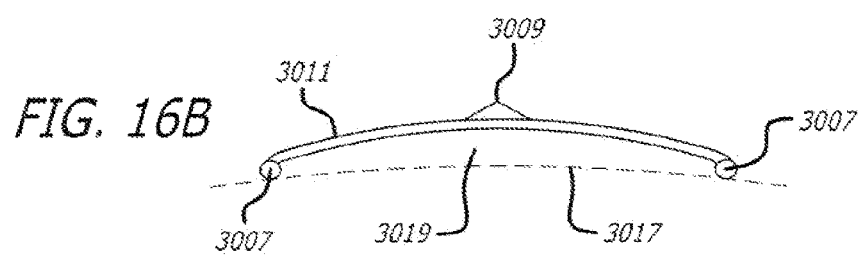

Referring to FIGS. 16A and 16B, one representative embodiment of an interface device 310 is shown. FIG. 16B shows a representative cross-sectional view of the device shown in FIG. 16A. Device 310 is one example of a device that can be utilized in accordance with the methods of the present invention in a minimally invasive manner. In the representative embodiment shown, the device 310 comprises a single wrap-around pad 315. In accordance with the novel "wrap-around" concept of the present invention, the device 310 is designed to wrap around the atrium of the heart. The embodiment of the device 310 shown in FIGS. 16A-16B can be used, for example, to wrap around the right atrium/portion of the heart of a patient, after minimally invasive implantation in a patient. It should be understood that a similar design molded to wrap around the left atrium/portion of the heart would involve the aspects of the device 310 reflected, as in a mirror image. The size and shape of the device 310 can also be varied as needed or desired, such that the device 310 can be used to wrap around another region of the heart of a patient, depending on whether there is another region of the heart that is afflicted with a cardiac rhythm disturbance.

In the embodiment shown, the device 310 includes a catheter 3003. The catheter 3003 is operable for delivering both electrical defibrillation (e.g., electric charge, via one or more conductive elements, similar to the conductive elements described in detail herein for device 10) and/or delivery of one or more pharmaceutical agents to a heart surface of a patient. Preferably, the catheter 3003 contains both a lumen 3400 (shown by the dotted lines in FIG. 16A; this lumen 3400 functions similar to the drug delivery channel 400, as described herein) and/or an electrically conductive braided shield 3005 (similar to the braided shield 115 described herein). In the case where electrical charge is not intended to be transferred to the patient heart, the requirement for a braided shield 3005 can be removed.

The lumen 3400 is used to deliver one or more pharmaceutical agents to a drug-delivery canal 3009 located within the pad 315.

The canal 3009 preferably runs down the center of the pad 315. The canal 3009 allows for drugs passing through the lumen 3400 to travel easily along the length of the pad 315 via the canal 3009 for targeted delivery to the heart surface. The device 310 can be designed such that one or more drugs (i.e. one or more pharmaceutical agents) delivered via the canal 3009 can be released at any site along the length of the canal 3009, in order to achieve the desired clinical effect and treatment of the patient.

In one embodiment of the present invention, the wrap material used to make the wrap-around pad 315 need not be electrically conductive. Alternatively, the wrap-around pad 315 can be constructed of an electrically conductive flexible material, which may also be elastic. One such material is a silicon rubber of low durometer (e.g. 30 Shore A) heavily doped with silver.

In the embodiment shown in FIG. 16A, the wrap-around pad 315 includes one or more electrically conductive "ribs" 3007 that are positioned along each side of the pad 315. Between each of these ribs 3007 is a flexible membrane 3011, which is preferably a thin flexible membrane. The thickness of the flexible membrane 3011 can be, for example, from about 0.01 inches to about 0.05 inches, preferably about 0.03 inches, and more preferably about 0.025 inches in thickness. The thickness can also be substantially uniform throughout the entire flexible membrane 3011.

The flexible membrane 3011 is well-suited for containing one or more pharmaceutical agents that are delivered via the canal 3009. In certain embodiments, the membrane 3011 is substantially permeable or at least semi-permeable to one or more pharmaceutical agents, in order to help achieve targeted delivery of the pharmaceutical agents to the intended heart surface. The membrane 3011 is also preferably electrically conductive and thereby conducts electric charge.

Preferably, each of the ribs 3007 are thicker, and contain more electrically conductive silver doping, and thereby conduct more electrical charge, as compared to the flexible membrane 3011. The electrical charge runs preferentially down the plurality of ribs 3007 of the pad 315. The one or more electrically conductive ribs 3007 are surprisingly useful in delivering an appropriate amount, frequency, and duration of electric charge to an intended heart surface, for example an atrial surface, for treatment of a cardiac rhythm disturbance such as, for instance, an arrhythmia. The ribs 3007 preferably provide substantially continual contact with the intended heart surface for transfer of electrical charge.

The ribs 3007 are also surprisingly useful for enabling a healthcare professional to stitch or otherwise fasten each rib 3007 to the heart surface of patient, when the device 310 is implanted in a patient in a minimally invasive manner.

FIG. 16B shows a representative cross-sectional view of the device shown m FIG. 16A. Referring to the cross sectional view shown in FIG. 16B, the flexible membrane 3011 preferably lays close to, or in contact with, or at least partially in contact with, the heart surface 3017. The dashedline in FIG. 16B schematically represents the heart surface 3017, for instance, the surface of an atrium.

As described herein, one or more pharmaceutical agents can be delivered via the device 310, such that the drugs (one or more pharmaceutical agents) passing through the lumen 3400 of the device 310 travel along the length of the pad 315 through the canal 3009 for targeted delivery to the heart surface.

In accordance with this preferred embodiment of the present invention, it has been surprisingly discovered that with the beating of the heart, the drugs can safely and easily pass from the canal 3009 through the membrane 3011, and thereafter the drugs can pass underneath the membrane 3011, and then the drugs can enter the space 3019 under the membrane 3011. The space 3019 is the space directly covering the heart surface 3017, and thus use of the canal 3009 and membrane 3011 in such a manner is surprisingly useful in allowing drugs to enter space 3019 and bathe the heart surface 3017. Thus, another unexpected advantage of the present invention is that the device 310 can be used to safely and reliably target the delivery of drugs within the desired space 3019, thus significantly reducing the amount of drug(s) required to achieve the desired clinical effect for the patient, and thus eliminating the serious problems associated with systemic toxicity from conventional treatments, as discussed in further detail herein.

As further shown in the cross-sectional view in FIG. 16B, the electrically-conductive ribs 3007 are preferably securely attached to the heart surface 3017, for instance, an atrial surface. The ribs 3007 can be attached to the heart surface 3017 by one or more stitches, staples, suitable adhesive or adhesives, and/or any other suitable attachment means. This attachment of the ribs 3007 to the heart surface 3017 also offers another surprising advantage: namely, this attachment allows the drugs delivered so be kept safely and reliably within the desired space 3019, thus allowing the drugs to bathe the heart surface 3017 to achieve the desired clinical effect.

Although not shown in the figures, it is to be understood that an interface device according to the present invention can be designed to include additional wrap-around pads 315, in addition to the single wrap-around pad 315 shown in FIG. 16A. For example, an interface device according to the present invention can include two wrap-around pads 315 designed with an appropriate configuration, thus enabling each wrap-around pad 315 to be wrapped around a different heart surface. Such an embodiment of the present invention would essentially function as a "multi-wrap" device. Although not shown in the figures, in this embodiment, multiple wrap-around pads 315 could be molded onto one catheter 3003 and/or lumen 3400 and/or braided shield 3005. The multiple wrap-around pads 315 would preferably be connected to a single catheter 3003 via a branch formed at the distal end of the catheter 3003. The multiple wrap-around, pads 315 could also be adjusted in shape, and/or scaled in size to be smaller or larger, as needed, or as deemed necessary by a healthcare professional, and this seating in size can be done on a patient-by-patient basis.

Referring again to FIG. 16A, although the device 310 is generally spiral-shaped, the device 310 can be designed with any other suitable shape, and can be formed of any suitable material or combination of materials.

The generally spiral shape of the device 310 is only one example. It is to be understood that device 310 can have any suitable shape, and is not limited to the generally spiral shape shown in FIG. 16A. When device 310 is placed over a region of a patient's heart, in a minimally invasive manner as described herein, the device 310 will not inhibit the beating of the heart. The device 310 can be placed in such a manner to facilitate drug delivery to the atrial surface of an atrium, or to another heart surface upon which the device 310 is placed. The device 310 can also optionally have an adhesive material on an underside thereof, in order to facilitate attachment of the device 310 to the heart surface. The device 310 can also be trimmed, cut or re-sized to any suitable size and shape prior to minimally invasive implantation in the patient, to correspond to the size of the patient's atrial surface area to which it will adhere. This procedure can be done on a patient-by-patient basis, since the needs of each patient may vary.

It is to be understood that the present invention contemplates any suitable variation on the size, shape, and dimensions of the various embodiments of the interface device of the present invention. In addition, the figures are intended to show only representative embodiments of the interface device; however, the scope of the present invention is not limited in any way by the examples or the figures shown and described herein.

According to another embodiment, the novel minimally invasive implantable device comprises at least one singularly electrical defibrillation interface, at least one singularly chemical defibrillation interface, or both an electrical and chemical defibrillation interface. According to yet other embodiments, the present invention includes utilization of existing electrical connections, and/or includes one or more external detection systems for detecting the electrical signals of the heart. These one or more detection systems cars be utilized in combination with the interface device of the present invention, in order to deliver the appropriate electrical defibrillation shock (e.g., electric charge) to the patient's heart, to achieve the desired clinical effect.

The novel minimally invasive implantable device of the present invention can by design interface with any suitable chemical and electrical delivery mechanisms currently in use in healthcare facilities.

In a preferred embodiment, the novel, minimally invasive implantable device of the present invention extends from the cardiac surface of the patient to outside the patient body, and does not impede the ability of the patient to move around. Thus, the present invention surprisingly and unexpectedly provides another advantage by not impeding the movement of the patient after the device has been implanted. The design of the present invention also surprisingly facilitates easy and convenient removal of the minimally invasive implantable device as further described herein.

In other embodiments, one or more modifications can be made to the interface device of the present invention. For example, one or more mechanical elements (for instance, one or more spring action wires) can be utilized with the device to enable one to safely and reliably position the plurality of leaflets 55 by a spring-open type of action, thus positioning the leaflets 55 as desired, after the device has been implanted.

In other embodiments, as discussed herein, the proximal portion 20 of the device 10 can be connected to a conveniently sized micro-pump (for instance, a micro-pump for drug delivery). The micro-pump can also be programmable, even wirelessly programmable, from outside of the chest well 40 of the patient, in order to safely, reliably and conveniently administer drugs as needed to treat the patient. The micro-pump can be implanted in a minimally invasive manner under the skin of the patient's chest wall, and will not impede the movement or other actions of the patient.

The present invention also surprisingly provides for much more convenient, easy, and minimally invasive removal of the novel minimally invasive implantable device after a designated period of time. For example, after a pre-specified period of time in which the minimally invasive implantable is used in an acute case (e.g., treating patients suffering from acute cases of abnormal cardiac rhythms), in which either chemical adhesives, dissolving stitches, or both have sufficiently degraded, a healthcare provider can simply, easily and conveniently remove the device of the present invention (e.g., the device 10) by simply pulling the device out of the patient body. This simple removal can be facilitated, for example, by grasping the end of the minimally invasive implantable device protruding from the patient body and pulling it out through the chest wall 40 and out of the patient body. In another embodiment, the minimally invasive implantable device (e.g., the device 10) can be pulled into itself, and then the entire minimally invasive implantable device can be reliably and efficiently removed from the patient body. The present invention thus provides for removal of the minimally invasive implantable device from the patient body with minimal intrusion and minimal invasiveness.

The minimally invasive implantable device of the present invention can be used for effective treatment of multiple categories of patients and indications, including various types of cardiac arrhythmias or abnormal cardiac rhythms. This includes, for instance, treatment of atrial fibrillation (AF) in patients suffering from chronic or acute onset AF that is intractable to conventional drug therapy.

According to certain preferred embodiments, the minimally invasive implantable device can be used in acute cases, in which patients suffer from acute cases of abnormal cardiac rhythms. In these cases, the novel minimally invasive implantable device transfers either electrical, chemical, or both forms of atrial defibrillation, as provided by chemical delivery and electrical delivery mechanisms, as described in further detail herein. The novel minimally invasive implantable device of the present invention interfaces the heart and transfers either electrical, chemical, or both forms of atrial defibrillation, as described in further detail herein.

The novel minimally invasive implantable device can by design easily, reliably and conveniently interface with any common chemical and electrical delivery mechanisms currently in use in healthcare facilities. Preferably, the novel minimally invasive implantable device extends form the cardiac surface(s) to outside the patient body, as patient-ambulatory considerations are minimized. This facilitates easy and convenient removal of an acute embodiment of the novel minimally invasive implantable device as described in U.S. Provisional Patent Application Ser. No. 61/743,759, the entire contents of which are incorporated herein by reference.

In one preferred embodiment, in patients suffering from acute cases of abnormal cardiac rhythms, two of the novel minimally invasive implantable devices of the present invention may be placed one each about the right and left atria. The two devices can safely and reliably transfer an electrical defibrillation shock generated outside the patient body, in a distributed fashion about each of the atria. Similarly, the two devices may transfer one or more pharmaceutical agents in a distributed fashion, "bathing" each of the regions with the one or more pharmaceutical agents.

The surprising benefits to this, in accordance with the present invention, include a significant reduction in the requisite electrical power that is required to pace the heart.

Thus, the present invention overcomes the many significant drawbacks and limitations associated with a conventional cardiac defibrillation lead (traditional leads are typically secured to the heart at a single point). There are also many other benefits of using the novel minimally invasive implantable devices of the present invention in such a manner. For instance, using the novel minimally invasive implantable device of the present invention in such a manner significantly reduces the amount or concentration of pharmaceutical agent(s) that is/are required to be utilized, by allowing targeted distribution of the pharmaceutical agent(s) about each of the atria, and maintaining the pharmaceutical agent within the region for extended periods of time, and thus also eliminating the systemic toxicity associated with conventional treatment approaches that utilize systemic delivery of drugs.

In other preferred embodiments, the minimally invasive implantable device of the present invention can be used in chronic cases, in which patients suffering from chronic abnormal cardiac rhythms can be assisted by the novel minimally invasive implantable device of the present invention which interfaces the heart and transfers either electrical, chemical, or both forms of atrial defibrillation.

In the chronic case, in which a patient suffers from chronic abnormal cardiac rhythms, the patient may not be undergoing a cardiac surgery prior to placement of the minimally invasive implantable device. In this case, according to one embodiment of the present invention, a minimally invasive implantable device of the present invention can be placed by less invasive surgical means, such as VATS (visually assisted thoracic surgery). Furthermore, this minimally invasive implantable device may transfer electrical, chemical, or both forms of defibrillation from either implanted devices and/or electrical and chemical sources external to the patient body.

In another embodiment, in the chronic case, in which a patient suffers from chronic abnormal cardiac rhythms, placement may include one novel minimally invasive implantable device over the right atrium and another novel minimally invasive implantable device placed about the back of the heart, in the region of the heart where the pulmonary veins enter. In this region, aberrant cardiac signals are often generated, as is the case with formation of scar tissue.

In either acute or chronic case, the novel interface device of the present invention transfers electrical, chemical, or both forms of defibrillation to the affected heart regions to facilitate defibrillation. The device of the present invention allows for significantly lower electrical energy and/or lower concentrations of pharmaceutical agent(s) as compared to conventional, external defibrillation means. In the acute case, two such novel devices may be placed one each about the right and left atria. Two devices can be used, in accordance with the present invention, to transfer an electrical defibrillation shock generated outside the patient body, in a distributed fashion about each of the atria. Similarly, the two devices may transfer one or more pharmaceutical agents in a distributed fashion "bathing" each of the regions with the agent(s).

Patients suffer routinely post cardiac surgery from abnormal cardiac rhythms. In these cases, the novel minimally invasive implantable device can be utilized for treatment of acute episodes of abnormal cardiac rhythms. According to one embodiment, the defibrillation device of the present invention can interface to the heart via a mechanism that is applied during surgery, and removed without surgery at a later date. The post-surgery scenario preserves the patient during the post-surgery healing phase.

According to other embodiments, the novel device may be utilized for intermittent use, "as needed" use, or for continuous use. The novel device of the present invention may also be utilized for asymmetric, dosing of heart chambers. Thus, according to certain embodiments, the dosing delivered to one heart chamber may differ from the dosing delivered to another heart chamber.

In accordance with the present invention, the novel, minimally invasive interface device accurately and reliably transfers either electrical defibrillation, chemical defibrillation, or both forms of defibrillation to the heart (e.g., the atria) to facilitate defibrillation, for instance, in either the acute case or chronic case. The minimally invasive interface device also surprisingly and unexpectedly allows for lower electrical power and/or lower concentrations of pharmaceutical agent(s) as compared to conventional, external defibrillation means.

The at least one pharmaceutical agents or drugs which may be delivered to the heart may include, for example, any combination of one or more drugs from suitable classes of pharmaceutical agents. As described elsewhere herein, it is to be understood that the term "pharmaceutical agent", as used herein, is intended to include, and therefore shall also be construed as also including, any and all pharmaceutically acceptable prodrugs, metabolites or derivatives of the pharmaceutical agent, and any and all pharmaceutically acceptable enantiomers, racemic forms, salt forms, free base forms, solvates, hydrates, hemihydrates, other hydrated forms, polymorphic or crystalline forms, isomorphs, or any other derivative thereof. Representative examples of at least one or snore pharmaceutical agents that can be used in accordance with the present invention are provided in further detail herein. Representative classes of pharmaceutical agents, include, but are not limited to, anti-arrhythmic agents, anesthetic agents, sedative agents, and/or other suitable agents.

In certain embodiments, an introducer tube (not shown) can be introduced through the chest wall of a patient in a minimally invasive procedure. Thereafter, the device of the present invention can be implanted through the introducer tube, and positioned over the intended cardiac surface (e.g., an atrial surface). After the device is implanted over the intended cardiac surface (e.g., an atrial surface), the introducer tube can easily be removed.

When used in accordance with the present invention, the goal of antiarrhythmic drug therapy is to restore normal rhythm and conduction in the patient. When it is not possible to revert to normal sinus rhythm, one or more pharmaceutical agents may be used in accordance with the present invention to prevent more serious and possibly lethal arrhythmias from occurring. Antiarrhythmic drugs may be used in accordance with the present invention to decrease or increase conduction velocity as needed: alter the excitability of cardiac cells by changing the duration of the effective refractory period; suppress abnormal automaticity; and to achieve other effects that contribute to a desired clinical outcome. The antiarrhythmic drugs may directly or indirectly alter membrane ion conductances, which in turn alters the physical characteristics of cardiac action potentials. A healthcare professional can determine what is appropriate when selecting the type, class, amount, dosage, dosing frequency, and other parameters when administering one or more pharmaceutical agents to a patient in accordance with the present invention.

For example, a healthcare professional may elect to administer one or more pharmaceutical agents with the effect of decreasing conduction velocity in order to help to abolish tachyarrhythmias caused by reentry circuits. Other types of antiarrhythmic drugs affect the duration of action potentials, and especially the effective refractory period. By prolonging the effective refractory period, reentry tachycardias can often be abolished. Because sympathetic activity can precipitate arrhythmias, a healthcare professional may elect to administer one or more pharmaceutical agents that block beta-adrenoceptors, which are used to inhibit sympathetic effects on the heart. Because beta-adrenoceptors are coupled to ion channels through defined signal transduction pathways, beta-blockers indirectly alter membrane ion conductance, particularly calcium and potassium conductance. Sometimes ventricular rate is excessively high because it is being driven by atrial flutter or fibrillation. Because it is very important to reverse ventricular tachycardia, one or more pharmaceutical agents may be administered to slow AV nodal conduction. Calcium channel blockers and beta-blockers may be selected for this indication, and may be administered to a patient in accordance with the present indication. In yet other examples, where appropriate in certain patients, one or more pharmaceutical agents can also be used to reduce AV conduction velocity in an attempt normalize ventricular rate during atrial flutter or fibrillation.

By way of example, certain representative classes of pharmaceutical agents that can be used in accordance with the present invention are listed below. These include certain representative classes of drugs that may be used in the treatment of arrhythmias. This list of pharmaceutical agents is given by way of example, and it is to be understood that the scope of the invention contemplates the use of any other suitable pharmaceutical agent, or one or more pharmaceutical agents, and these one or more other pharmaceutical agents can easily and reliably be selected and determined by the skilled artisan without any undue experimentation.

These representative classes of pharmaceutical agents include certain antiarrhythmic drug classes. The pharmacology and properties of all or these representative classes has been well characterized and thus it would be straightforward (and not require undue experimentation) for a healthcare professional to determine the suitable amount, dosing/dosage schedule and frequency of administration of these agents using the devices and methods of the present invention in order to achieve the desired clinical effects. Examples of suitable antiarrhythmic drug classes that can be used in accordance with the present invention include:

Class I—Sodium-channel blockers
Class II—Beta-blockers
Class III—Potassium-channel blockers
Class IV—Calcium-channel blockers Class I (Class IA, IB and IC)—Representative Sodium Channel Blockers By way of example, the following table lists representative Class I agents that can be used clinically in accordance with the present invention. The table below also lists, by way of example, certain representative therapeutic uses of these agents.

Examples of Class IA agents: representative uses include treatment of atrial fibrillation, flutter; supraventricular & ventricular tachyarrhythmias quinidine, procainamide, disopryamide
Examples of Class IB agents: representative uses include treatment of ventricular tachyarrhythmias lidocaine, tocainide, mexiletine
Examples of Class IC agents: representative uses include treatment of supraventricular tachyarrhythmias and ventricular tachyarrhythmias flecainide, propafenone, moricizine Class II—Representative Beta-Blockers By way of example, the following table lists representative beta-blockers that can be used clinically in accordance with the present invention. These include 1) non-selective blockers (block both $\beta_1$ and $\beta_2$ receptors), or 2) relatively selective $\beta_1$ blockers ("caidioselective" beta-blockers). Some beta-blockers are known to have additional mechanisms besides beta-blockade that, contribute to their unique pharmacologic profile. Representative agents from the two classes of beta-blockers are listed in the following table for illustration purposes only.

Examples of Non-selective $\beta_1/\beta_2$ blockers for treatment of arrhythmias nadolol, propranolol, sotalol, timolol
Examples of representative $\beta_1$-selective blockers for treatment of arrhythmias acebutolol, atenolol, betaxolol, bisoprolol, esmolol, metoprolol Class III—Representative Potassium-Channel Blockers By way of example, the following table lists representative Class III compounds (potassium-channel blockers) that can be used clinically in accordance with the present invention, and also lists certain representative therapeutic uses.

| Drug | Representative Therapeutic Uses |
| --- | --- |
| amiodarone | ventricular tachycardia, including ventricular fibrillation: atrial fibrillation and flutter |
| dronedarone | atrial fibrillation (non-permanent) and flutter |
| bretylium | ventricular tachycardia and fibrillation |
| sotalol | ventricular tachycardia; atrial flutter and fibrillation |
| ibutilide | atrial flutter and fibrillation |
| dofetilide | atrial flutter and fibrillation |

Class IV—Representative Calcium-Channel Blockers (CCBs)

The pharmacology and antiarrhythmic properties of calcium-channel blockers (CCBs) are well known, and are related primarily to their ability to decrease the firing rate of aberrant pacemaker sites within the heart, and are also related to their ability to decrease conduction velocity and prolong repolarization, especially at the atrioventricular (/AV) node. This latter action at the atrioventricular (AV) node helps to block reentry mechanisms, which can cause supraventricular tachycardia. Representative CCBs that can be used in accordance the present invention include, for example, verapamil (phenylalkylamine class), which is relatively selective for the myocardium, and can be used to treat arrhythmias in patients. Diltiazem (benzothiazepine class) is another example of a CCB agent that is relatively intermediate between verapamil and dihydropyridines in terms of its selectivity for vascular calcium channels. It is to be understood that these are only a few of the many examples of CCB agents that can be used in accordance with the present invention.

In certain representative embodiments, pharmaceutical agents that can be used in accordance with the present invention include for example, at least one anti-arrhythmic drug such as, for example, procainamide, amiodarone, a combination of procainamide and at least one other anti-arrhythmic drug, a combination of amiodarone and at least one other anti-arrhythmic drug, or a combination of procainamide, amiodarone and at least one other anti-arrhythmic drug. Further, the at least one drug may also comprise at least one anesthetic drug such as, for example, procaine, lidocaine, a combination of procaine and at least one other anesthetic drug, a combination of lidocaine and at least one other anesthetic drug, or a combination of procaine, lidocane, and at least one other anesthetic drug.

Exemplary pharmaceutical agents may include anti-arrhythmic drugs such as, for example, a procainamide and amiodarone. Alternatively or additionally, the drugs may include anesthetic drugs such as, for example, procaine and lidocaine.

The at least one pharmaceutical agent may be administered continuously (by, for example, an infusion pump) or as a bolus. Further, administration of the at least one drug may be automated with respect to a monitored level of the drug's concentration and/or in response to a perceived need such as, for example, in response to detecting atrial fibrillation.

In certain situations, pharmaceutical agents delivered through the drug delivery channel 400 may enhance defibrillation and/or provide local anesthesia to the atrium before an electric shock, thereby reducing the discomfort suffered by a patient during the shock. Electric shock would of course be administered in individual cases only if deemed necessary by a healthcare professional.

As the atrial walls are thin and outlined with a loose epithelial layer, the anti-arrhythmic drugs will readily infiltrate the atrial tissue thereby enabling the drugs to prevent and/or stop atrial fibrillation. Further, by delivering the anti-arrhythmic drugs through the drug delivery channel 400 and directly to the atrial walls, the atrial walls may be saturated without experiencing the systemic toxicity associated with conventional systemic treatment.

As described herein, in accordance with the present invention, the novel minimally invasive implantable device transfers either electrical, chemical, or both forms of defibrillation to the atria to facilitate defibrillation, for instance, in either the acute case or chronic case.

The novel minimally invasive implantable device can transfer pharmaceutical agents to the atria to facilitate defibrillation. Any suitable dose or dosage range of one or more pharmaceutical agents can be transferred to the atria to facilitate defibrillation. The determination of suitable dose or dosage range of one or more pharmaceutical agent will typically be determined by a healthcare professional, and will typically depend on the needs of the particular patient that is being treated.

Any suitable dose and dosage ranges of one or more pharmacologic agent can be used in accordance with the present invention are described herein. Certain examples are provided herein, and shall not be construed as limiting the scope of the invention in any way, and again are provided for illustrative purposes only.

ADDITIONAL REPRESENTATIVE EXAMPLE

Delivery of Drugs to the Heart

According to preferred embodiments of the invention, one or more algorithms may be used, for example, to control and program the operation of the interface device of the present invention. For example, one or more algorithms may be used, for example, to control and program an operation whereby one or more pharmaceutical agents are delivered via the interface device of the present invention to the intended region(s) of the heart of a patient. As further described herein, the drugs (pharmaceutical agents) that are delivered to the heart may include any number of suitable types of drugs, for example, one or more anesthetics, sedatives, and/or other classes of pharmaceutical agents, or any combination thereof. The means by which these drugs are transferred to the interface device of the present invention may include, for example, the use of one or more algorithms whereby the active drug(s) are pulsed into the interface device along with other agents such as (for example) saline, heparin, antibiotic, and others, such that a pulse width modulation exists. In one representative scenario, during acute defibrillation, the amount of pharmaceutical agent may be increased relative to the other drugs per period of time. According to certain embodiments, a positive pressure within the minimally invasive implantable device of the present invention can be maintained, thus preventing clotting and clogging, and also preventing interruption at critical periods during treatment.

Still other objects and advantages of preferred embodiments of the present invention will become readily apparent to those skilled in the art from the description herein, wherein there is described certain examples for illustrative purposes. It is to be understood that the present invention is capable of modification in various respects, all without departing from the spirit and scope of the invention. Accordingly, the description herein should be regarded as illustrative in nature, and not as restrictive, and not as limiting the scope of the present inventions in any respect.

It should be understood that the exemplary embodiments described herein should be considered in a descriptive sense only and not for purposes of limitation. It is understood by those skilled in the art that changes may be made in these embodiments without departing from the principles and spirit of the invention, the scope of which is defined in the claims and their equivalents.

Example 1

In this example, the present invention has been shown to be effective for targeted, local administration of the drugs amiodarone, sotalol, and procainamide directly into cardiac tissue postoperatively at a fraction of the systemic dosages using conventional approaches. In this example, Table 1 below lists these drugs, the postoperative oral and intravenous dosages (administered by conventional treatments) and, by comparison, dosages used for the targeted tissue delivery form of therapy using the devices of the present invention. As can be seen from Table 1, significantly less drug is required for treatment when the present invention is used for targeted delivery of the drugs, which also means that there is significantly less systemic toxicity when the present invention is used.

It is to be understood that Table 1 is provided for exemplary purposes, and describes representative drugs and dosages used in accordance with certain embodiments of the present invention. In no way whatsoever is Table 1 meant to limit the scope of the present invention. It is therefore to be understood that the present invention is capable of being used with other drugs and at other dosages, in accordance with other embodiments of the present invention.

TABLE 1

Representative Antiarrhythmic Drug Therapy Protocol

| Drug | Orally (Postoperative) | IV (intravenous) (Postoperative) | Exemplary dosages used for the targeted tissue delivery form of therapy using the present invention |
|---|---|---|---|
| Amiodarone | 400 mg daily until discharge, or 200 mg daily × 1 month after discharge | 150 mg IV over 2 min. then 1 mg/min × 6 h, then 0.5 mg/min × 18 h | Less than 10% of the systemic dose |
| Sotalol | 80 mg orally 2 × daily (<70 kg) 120 mg orally 2 × (>70 kg) | Infuse 75 mg over 5 hours by intravenous route every 12 hours | Less than 10% of the systemic dose |
| Procainamide | N/A in United States | Loading dose: 15 to 18 mg/kg administered as slow infusion over 25-30 minutes or 100 mg/dose at a rate not to exceed 50 mg/minute repeated every 5 minutes as needed Maintenance dose: 1 to 4 mg/min by continuous infusion. | Less than 10% of the systemic dose |

Example 2

Studies were conducted to determine the differences between intrapericardial (IPC) drug delivery versus intravenous (IV) drug delivery of the antiarrhythmic drug procainamide. In one study, using two groups of swine, investigators administered procainamide intravenously (n=6) or primordially (n=7) using sequential intravenous doses of 2, 8, 16 mg/kg (cumulative was 2, 10, 26 mg/kg) or sequential pericardial doses of 0.5, 1, and 2 mg/kg (cumulative was 0.5, 1.5, 3.5 mg/kg). Each dose was re-suspended in 10 ml and administered at a rate of 1 mL/min. The pharmacokinetics of the two drug delivery methods was statistically significant. Pericardial delivery produced peak drug concentrations within the range of 250 to 900 ug/ml while the measurable level for plasma concentration was low (<1 ug/mL). The intravenous delivery yielded peak plasma concentrations ranging from <1 to 40 ug/mL and the concentrations within the pericardial fluid were equal to that of the plasma concentration. It should be noted that the pericardial fluid concentration during intravenous delivery was 100 times less than that of intrapericardial delivery. The atrial electrophysiologic values were similar between both sets of delivery methods, indicating a lower direct dose can achieve similar therapeutic responses. The 3.5 mg/kg cumulative pericardial dose increased right atrial ERP by 22% from the baseline, while the 10 and 26 mg/kg cumulative intravenous doses prolonged atrial ERP by 24% and 18%, respectively. In addition, the cumulative doses of 3.5 mg/kg (pericardial) and 26 mg/kg (intravenous) prevented atrial fibrillation induction in 71% and 83% of the animals, respectively. In terms of ventricular electrophysiological properties, pericardial delivery had no significant effects on ventricular electrophysiology, heart rate, or systemic blood pressure. However, the 26 mg/kg intravenous injected procainmide dose prolonged atrial ventricular conduction times and reduced both interventricular conduction (RV and LV activation) indicating that intravenous delivery can affect the entire heart while IPC specifically targets the atria. In addition, investigators conducted a single pericardial dose of 2 mg/kg in 5 additional animals and results were similar to the cumulative dosing in terms of effects on electrophysiology and pharmacokinetics. This representative study shows that lower drug doses (approximately 10× lower) delivered IPC can affect atrial electrophysiology to the same extent as higher dosed IV injections while not affecting ventricular electrophysiology.

In addition to the embodiments described herein, the device and methods described herein are not limited to treatment of atrial fibrillation. The device and methods of the present invention may also be used, for example, to treat ventricular fibrillation. It should be understood that the apparatus and methods described herein are illustrative only. It should therefore be understood that the description herein relates only to certain embodiments of the present invention and that numerous modifications or alterations can be made therein without departing from the spirit and the scope of the present invention as set forth in the following claims.

That which is claimed is:

1. A minimally invasive device for treatment of a patient, the device comprising:
   a. at least one inner catheter adapted to deliver a drug to a cardiac surface of the patient;
   b. an outer catheter substantially surrounding the at least one inner catheter;
   c. a plurality of electrically conductive elements within the inner catheter and extending to be also located at a substantially distal portion of the device; and
   d. at least one membrane interconnecting the plurality of electrically conductive elements at the substantially distal portion of the device,
   wherein the plurality of electrically conductive elements are adapted to provide defibrillation energy to a cardiac surface of the patient.

2. The device according to claim 1, wherein the device further comprises at least one drug delivery channel located within the inner catheter and adapted to deliver of at least one drug to the cardiac surface or the patient.

3. The device according to claim 1, wherein the plurality of electrically conductive elements are arranged in a flower-like arrangement fanning out from a central hub.

4. The device according to claim 2, wherein the plurality of electrically conductive elements surround the drug delivery channel.

5. The device according to claim 4, wherein at least one adhesive material is provided on an underside of the membrane.

6. The device according to claim 5, wherein the at least one adhesive material comprises at least one adhesive polymer.

7. The device according to claim 2, further comprising at least one drug comprises at least one antiarrhythmic drug.

8. The device according to claim 7, wherein the at least one antiarrhythmic drug is selected from the group consisting of procainamide, amiodarone, a combination of procainamide and at least one other antiarrhythmic drug, a combination or amiodarone and at least one other antiantiarrhythmic drug, and a combination of procainamide, amiodarone and at least one other anti-arrhythmic drug.

9. The device according to claim 2, wherein at least one drug further comprises at least one anesthetic drug.

10. The device according to claim 9, wherein the anesthetic drug is selected from the group consisting of procaine, lidocaine, a combination of procaine and at least one other anesthetic drug, a combination of lidocaine and at least one other anesthetic drug, and a combination of procaine, lidocaine, and at least one other anesthetic drug.

11. A method of treating a patient suffering from an abnormal cardiac rhythm, the method comprising
   (i) implanting a minimally invasive device, the device comprising:
   a. at least one inner catheter adapted to deliver a drug to a cardiac surface of the patient;
   b. an outer catheter substantially surrounding the at least one inner catheter;
   c. a plurality of electrically conductive elements within the inner catheter and extending to be also located at a substantially distal portion of the device; and
   d. at least one membrane interconnecting the plurality of electrically conductive elements at the substantially distal portion of the device,
   (ii) delivering defibrillation energy to a cardiac surface of the patient with the plurality of electrically conductive elements,
   wherein the distal portion of the device further comprises at least one drug release site for delivery of at least one drug to the cardiac surface of the patient.

12. The method according to claim 11, wherein the plurality of electrically conductive elements are arranged in a flower-like arrangement fanning out from a central hub.

13. The method according to claim 11, wherein the device further comprises at least one drug delivery channel located within the inner catheter and adapted to deliver of at least one drug to the cardiac surface or the patient and wherein the plurality of electrically conductive elements surround the drug delivery channel.

14. The method according to claim 11, wherein at least one adhesive material is provided on an underside of the membrane.

15. The method according to claim 11, further comprising (iii) delivering at least one drug to the cardiac surface of the patient.

16. The method according to claim 15, wherein the at least one drug comprises at least one antiarrhythmic drug.

17. The method according to claim 16, wherein the at least one antiarrhythmic drug is selected from the group consisting of procainamide, amiodarone, a combination of procainamide and at least one other anti-arrhythmic drug, a combination of amiodarone and at least one other antiarrhythmic drug, and a combination of procainamide, amiodarone and at least one other anti-arrhythmic drug.

18. The method according to claim 15, wherein the at least one drug comprises at least one anesthetic drug.

19. The method according to claim 18, wherein the anesthetic drug is selected from the group consisting of procaine, lidocaine, a combination of procaine and at least one other anesthetic drug, a combination of lidocaine and at least one other anesthetic drug, and a combination of procaine, lidocaine, and at least one other anesthetic drug.

* * * * *